United States Patent
Abramov

(10) Patent No.: US 11,931,199 B2
(45) Date of Patent: Mar. 19, 2024

(54) NOZZLES FOR AMPLIFYING AND SUPPRESSION OF SOUND

(71) Applicant: Yuri Abramov, Holon (IL)

(72) Inventor: Yuri Abramov, Holon (IL)

(*) Notice: Subject to any disclaimer, the term of this patent is extended or adjusted under 35 U.S.C. 154(b) by 370 days.

(21) Appl. No.: 17/160,429

(22) Filed: Jan. 28, 2021

(65) Prior Publication Data

US 2022/0240888 A1 Aug. 4, 2022

(51) Int. Cl.
| | | |
|---|---|---|
| G10K 11/08 | (2006.01) | |
| A61B 7/02 | (2006.01) | |
| B05B 1/06 | (2006.01) | |
| F15D 1/00 | (2006.01) | |
| G10K 11/16 | (2006.01) | |
| G10K 11/26 | (2006.01) | |

(52) U.S. Cl.
CPC .............. *A61B 7/02* (2013.01); *G10K 11/08* (2013.01); *G10K 11/161* (2013.01); *G10K 11/26* (2013.01)

(58) Field of Classification Search
CPC ...... G10K 11/025; G10K 11/08; G10K 11/16; G10K 11/161; G10K 11/26; F15D 1/12; F15D 1/00; F15D 1/08; B05B 1/06
See application file for complete search history.

(56) References Cited

U.S. PATENT DOCUMENTS

| | | | | |
|---|---|---|---|---|
| 3,230,923 A | * | 1/1966 | Hughes | G10K 5/02 116/137 A |
| 4,592,509 A | * | 6/1986 | Moss | B05B 1/005 239/425.5 |
| 5,060,867 A | * | 10/1991 | Luxton | F15D 1/08 431/9 |
| 6,523,991 B1 | * | 2/2003 | Maklad | B01F 25/31242 137/890 |
| 8,402,745 B2 | * | 3/2013 | Denne | F02K 7/04 60/247 |
| 9,739,296 B2 | * | 8/2017 | Schlosser | F41A 21/30 |
| 10,928,146 B2 | * | 2/2021 | Van Donkelaar | F41B 11/60 |
| 11,493,066 B2 | * | 11/2022 | Abramov | F01D 5/141 |
| 11,499,525 B2 | * | 11/2022 | Abramov | F03D 3/0454 |
| 2017/0316133 A1 | * | 11/2017 | Abramov | G06F 30/17 |
| 2018/0266394 A1 | * | 9/2018 | Abramov | F02K 1/00 |
| 2019/0280561 A1 | * | 9/2019 | Abramov | H02K 7/183 |

FOREIGN PATENT DOCUMENTS

| | | | | |
|---|---|---|---|---|
| AU | 2018204546 B2 | * | 12/2019 | ............. F02K 1/00 |
| CN | 112424444 A | * | 2/2021 | ......... E21B 41/0078 |
| GB | 2546834 A | * | 8/2017 | ............. F02K 7/00 |
| JP | 2004529580 A | * | 9/2004 | |
| WO | WO-9201602 A1 | * | 2/1992 | |

* cited by examiner

*Primary Examiner* — Edgardo San Martin

(74) *Attorney, Agent, or Firm* — Bay State IP, LLC

(57) ABSTRACT

The invention discloses a novel passive sound transformer, either a sound-booster or a sound-silencer, embodied as an acoustic waveguide, a specific shape of which provides for either amplifying the intensity of acoustic waves at the expense of both the heat energy and the concomitant turbulence of moving fluid wherein the amplified intensity of the acoustic waves is manifested as sound loudness boosting or, contrarywise, transforming the wave power of elastic waves into the heat of the ambient fluid.

7 Claims, 9 Drawing Sheets

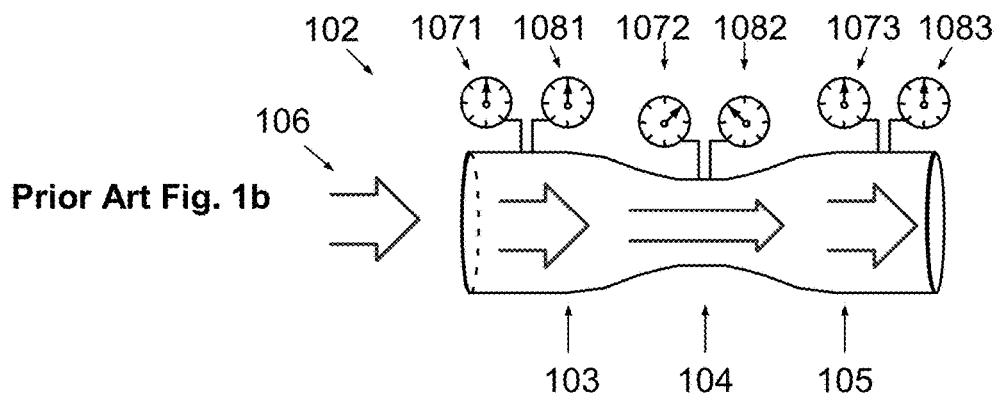
Prior Art Fig. 1b
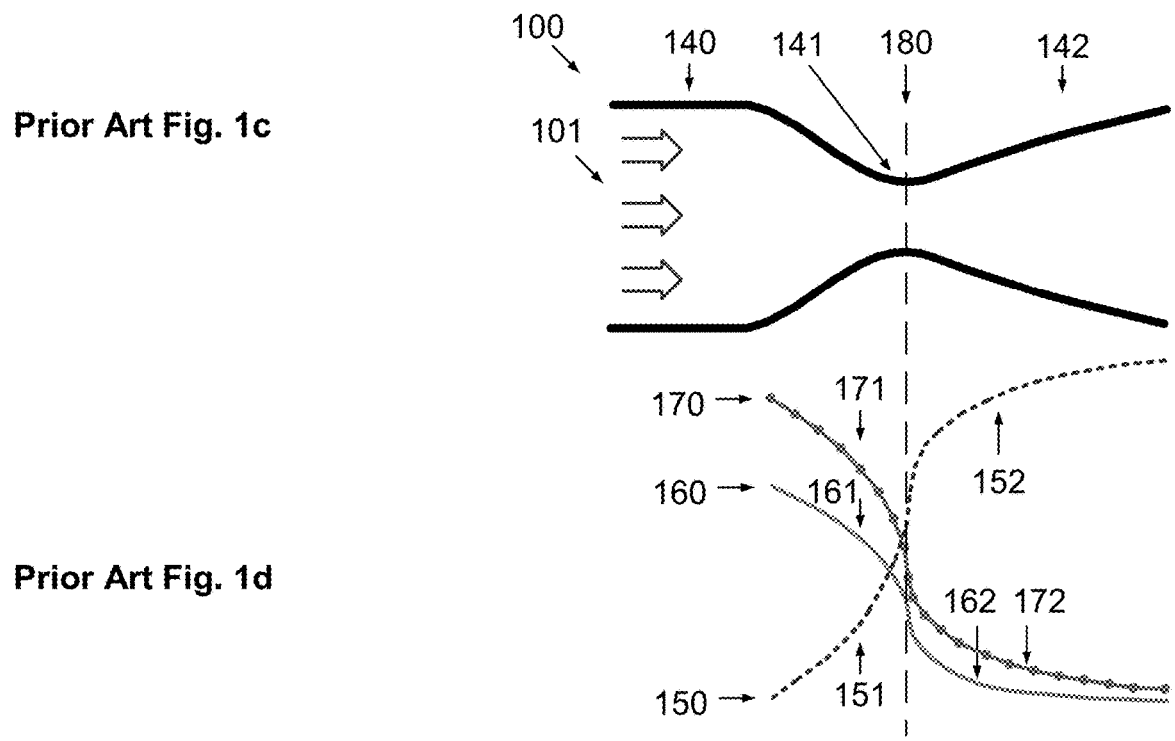
Prior Art Fig. 1c
Prior Art Fig. 1d

Prior Art Fig. 1e
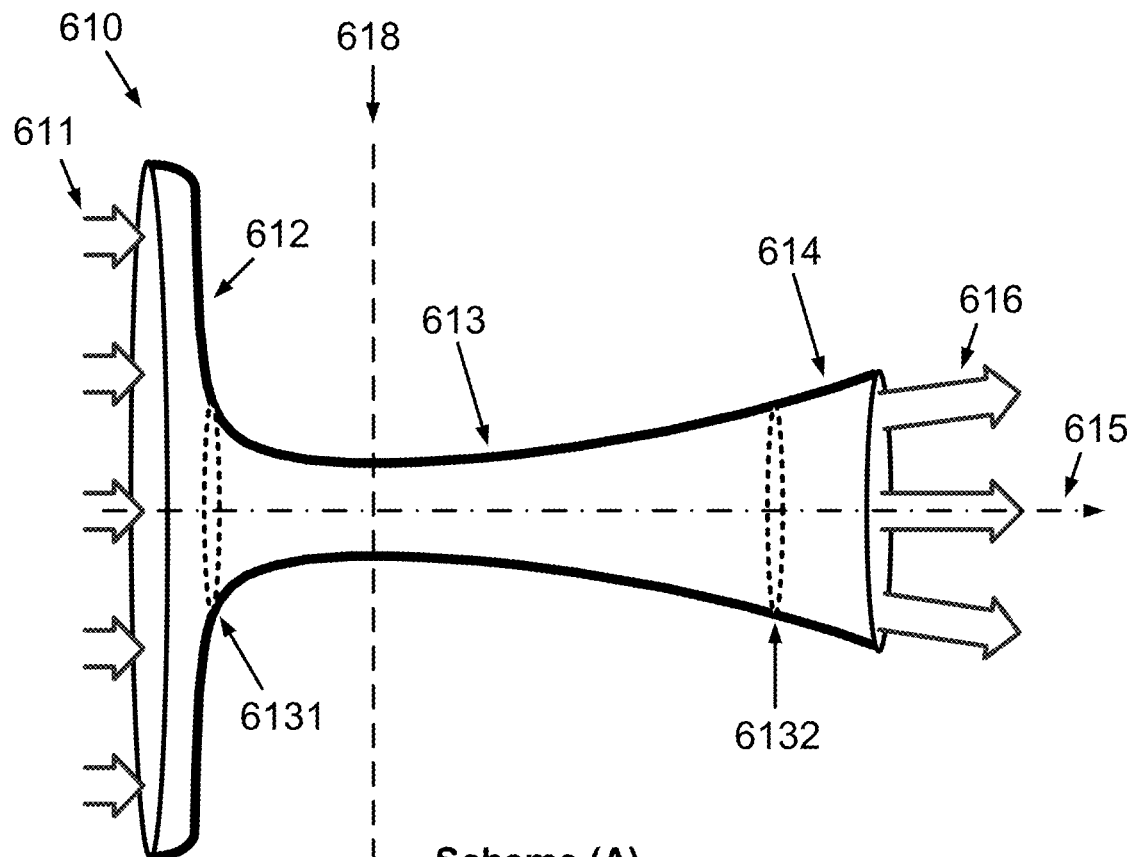
Scheme (A)
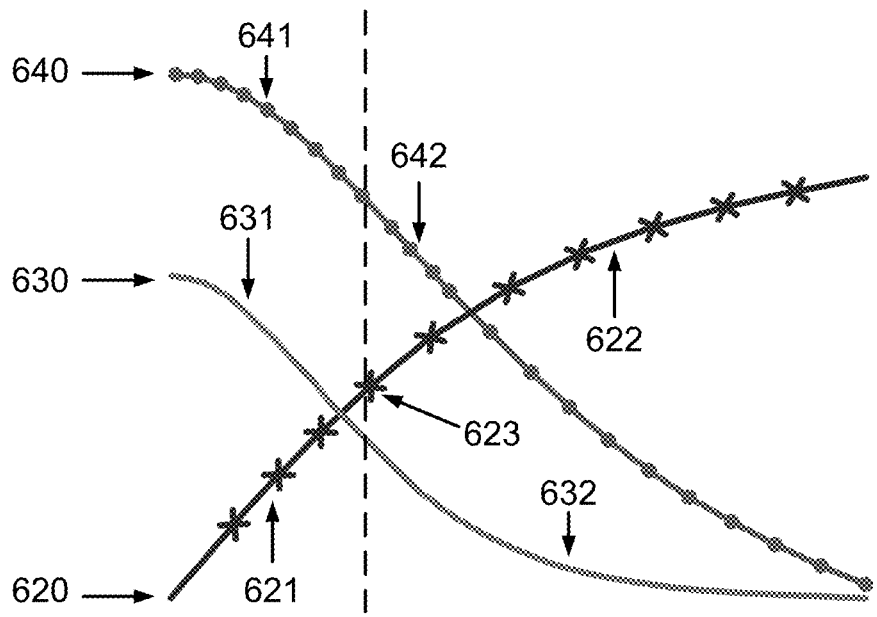
Graph (B)

Prior Art Fig. 1f
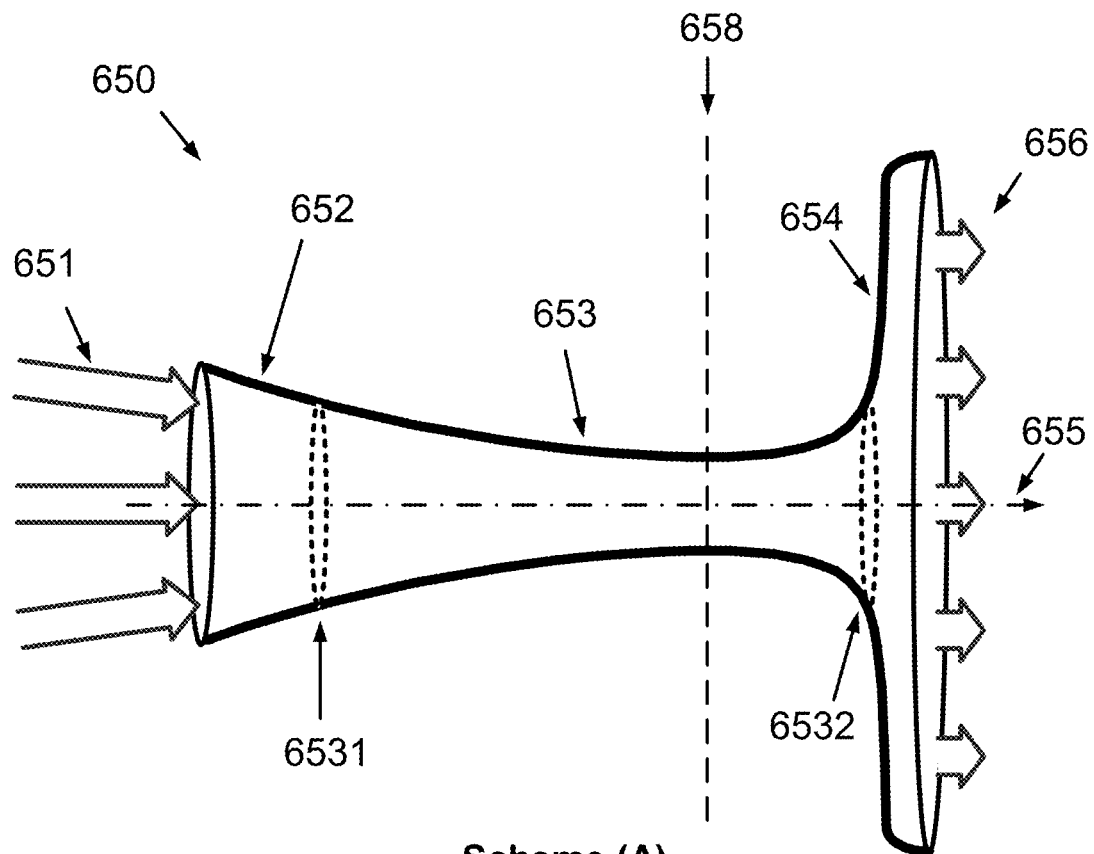
Scheme (A)
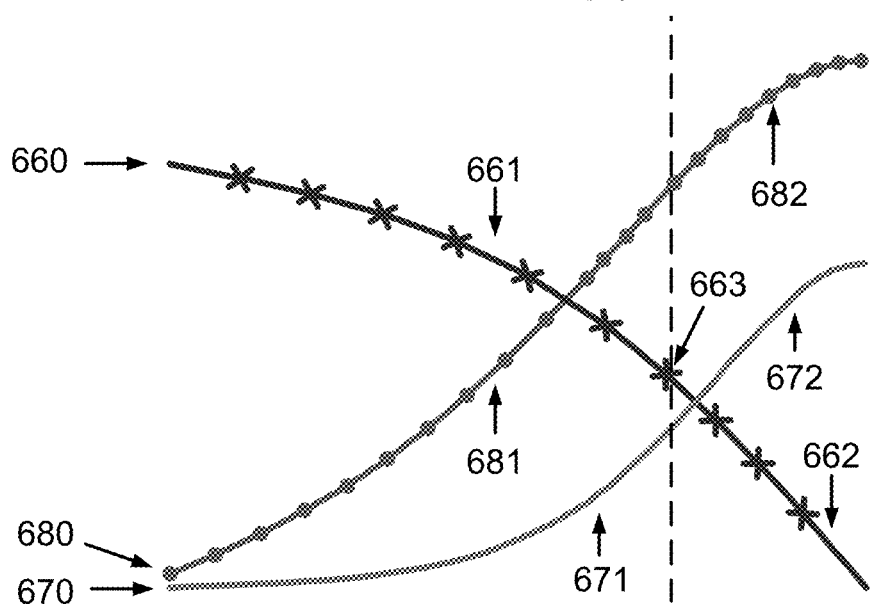
Graph (B)

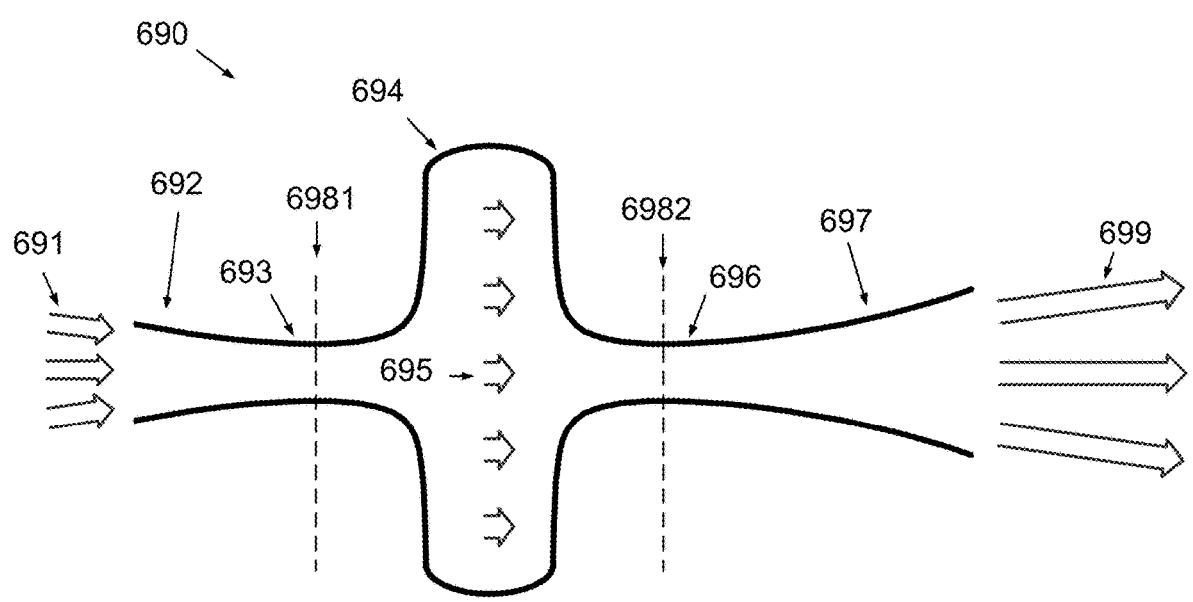
Prior Art Fig. 1g

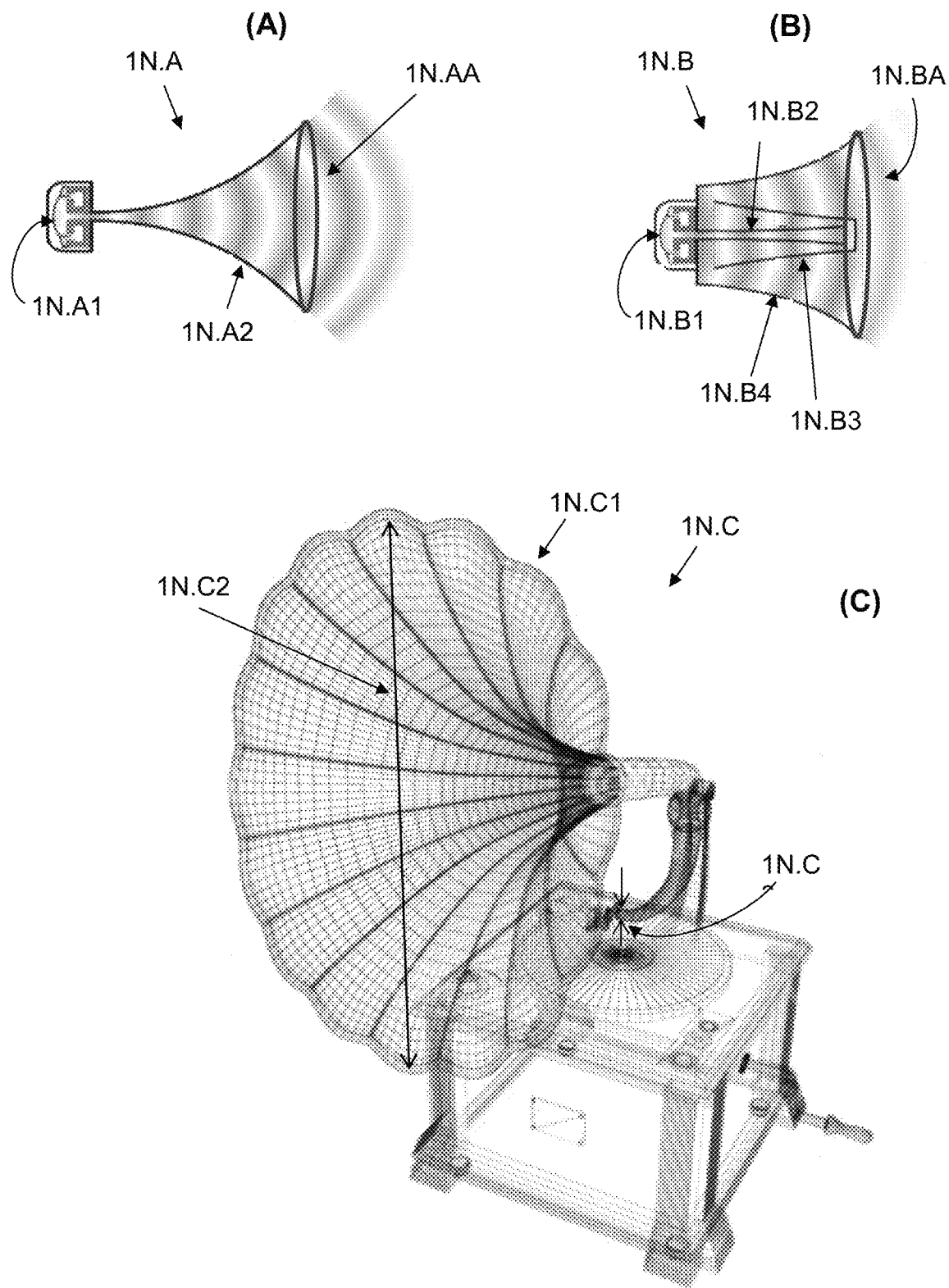
Prior Art Fig. 1n

Prior Art Fig. 1L
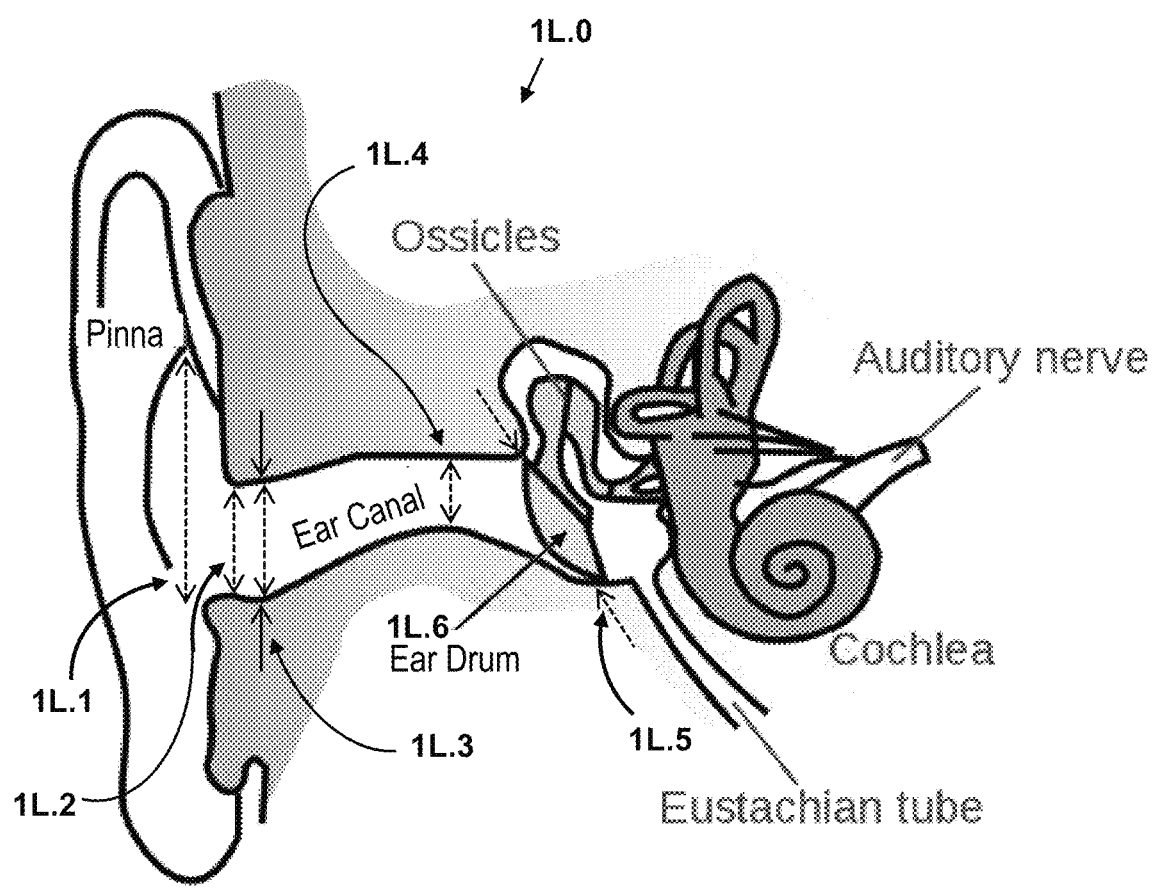

Fig. 2 Case (A)
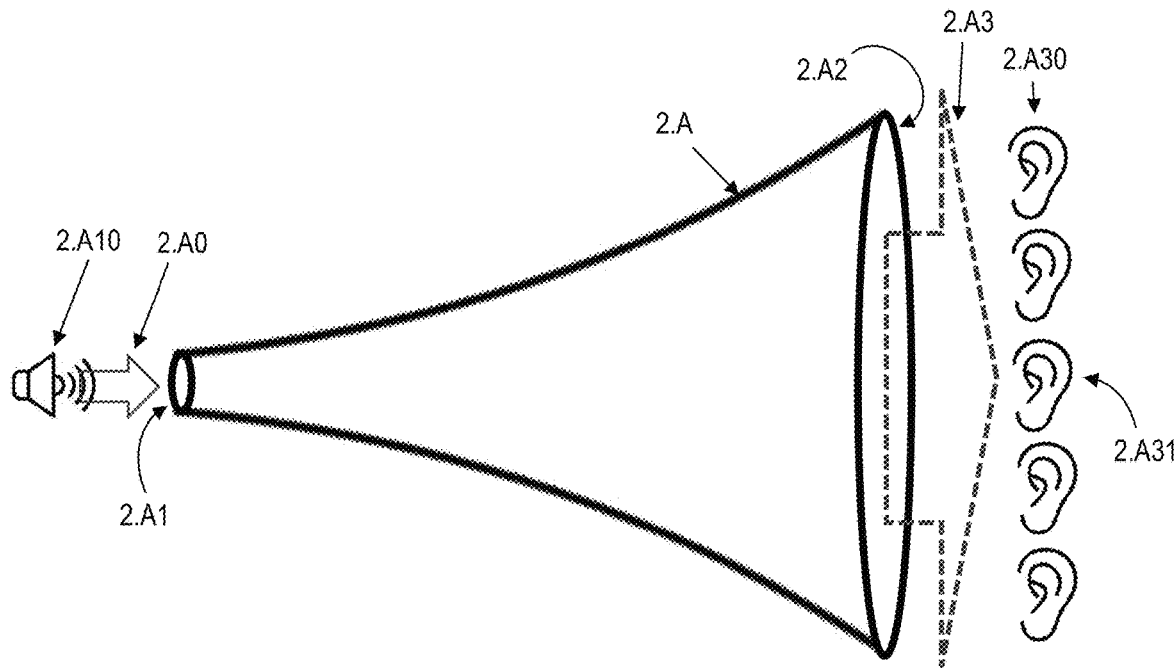
Fig. 2 Case (Cascade)
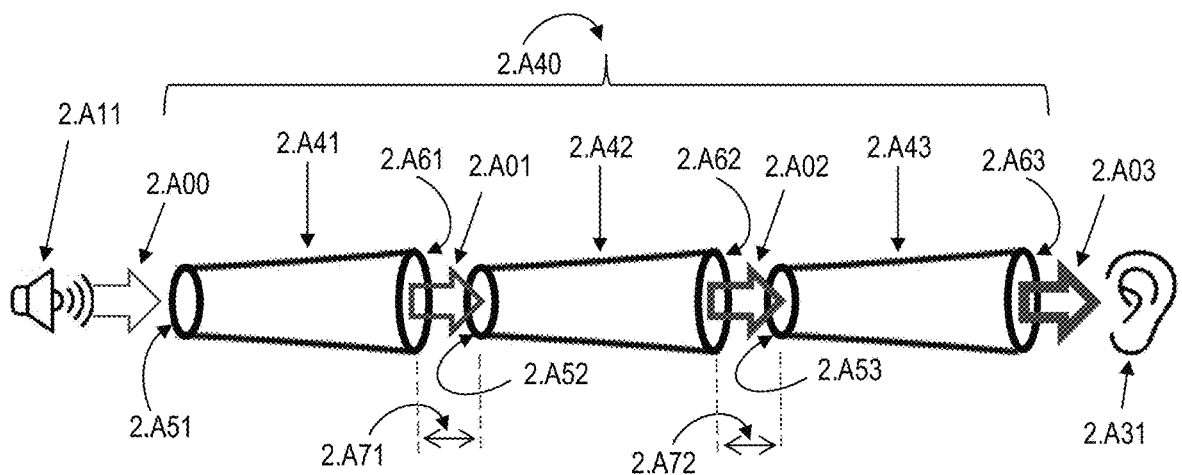

Fig. 2 Case (B)
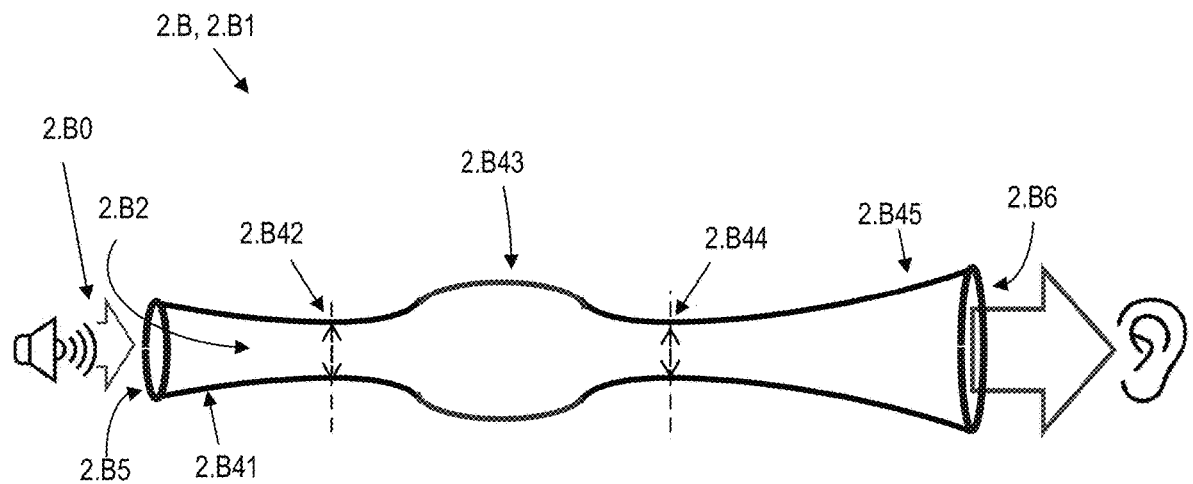
Fig. 2 Case (C)
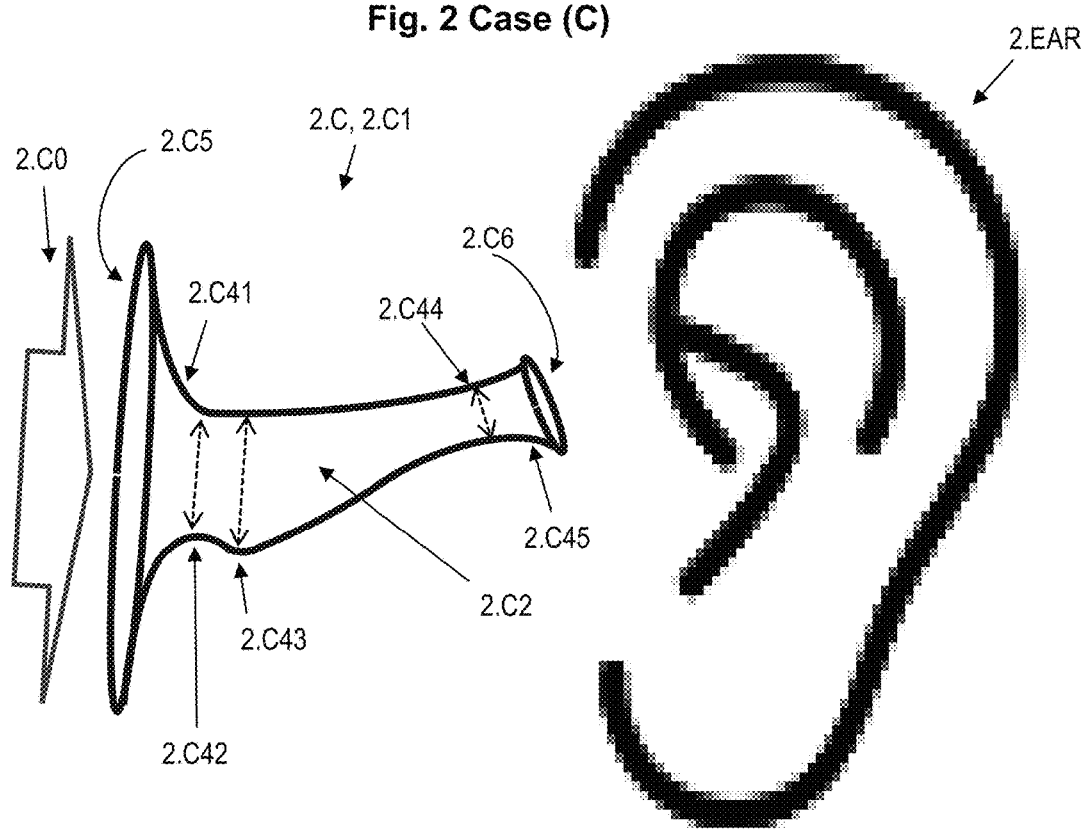

Fig. 3
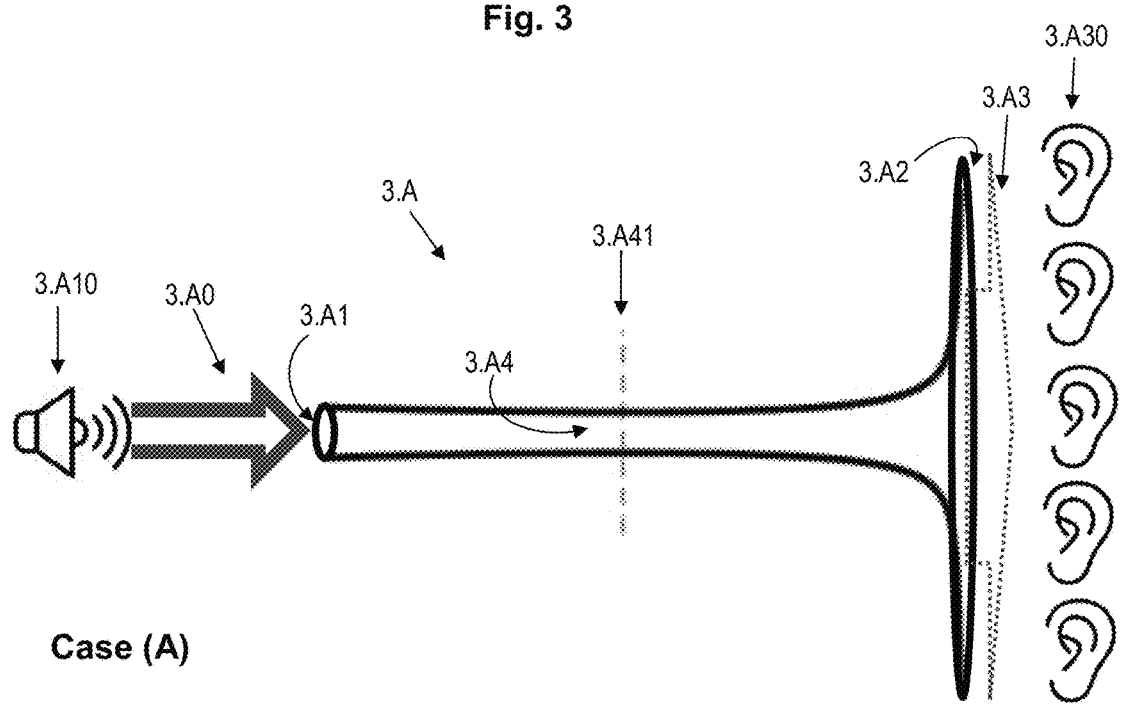
Case (A)
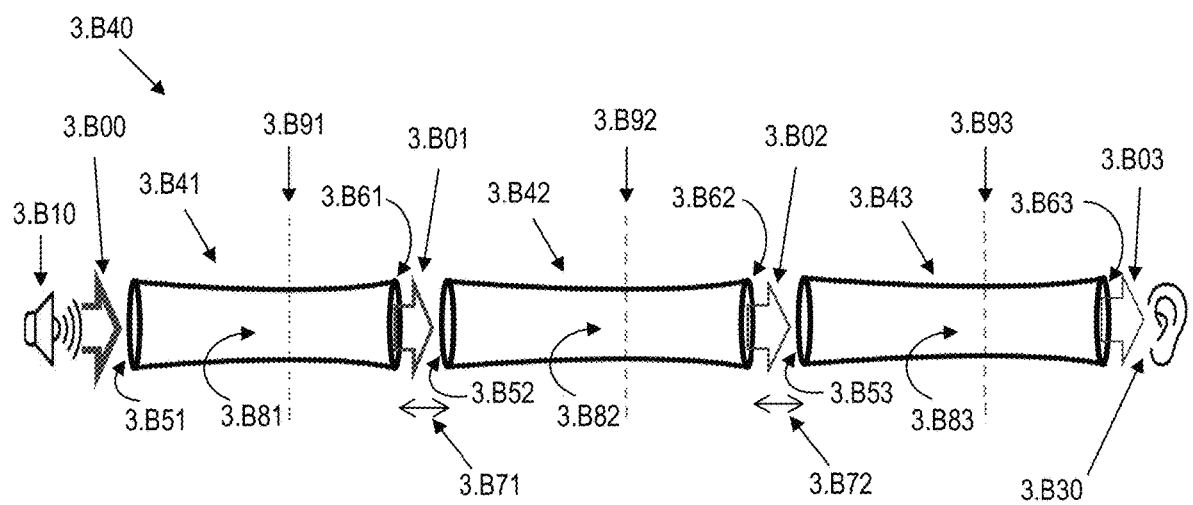
Case (B)

NOZZLES FOR AMPLIFYING AND SUPPRESSION OF SOUND

FIELD OF THE INVENTION

The invention, generally, relates to fluid dynamics and the use of jet-effect applied to elastic waves propagating in fluid, and, more particularly, relates to the use of the jet-effect for designing a jet-nozzle utilized as a passive sound transformer and applied to boost and/or suppress the sound loudness.

BACKGROUND OF THE INVENTION

The following issued patents and publications provide potentially relevant background material, and are herein incorporated by reference in their entirety:

GB2546834 by Abramov, further indicated by A01,
US 20190280561 by Abramov, further indicated by A02,
AU 2018204546 by Abramov, further indicated by A03, In the mentioned prior art AU01, AU02, and AU03, the equation of molecular fluid motion is applied to disclose an airfoil nozzle and wing.

In this patent application, a passive sound transformer, either amplifier or suppressor, is disclosed; the passive sound transformer is embodied as either: a divergent horn, or a convergent-divergent pipe, or a two-stage convergent-divergent nozzle, or a piecewise-divergent pipe, or a piecewise-convergent-divergent pipe, all are specifically shaped.

The inventor points out to:

On the one hand, a diversity of manifestations of the Venturi effect and the de Laval jet-effect, both resulting in a phenomenon of convective self-acceleration, wherein there is the feature of self-extra-acceleration of a flow within a de Laval jet-nozzle; and On the other hand, a diversity of waving jet-effect, namely to:

a feature that, as shown in the book "The Feynman Lectures on Physics", volume 1, chapter 30 "Diffraction" by Richard P. Feynman, Robert B. Leighton, and Matthew Sands, the intensity (the wave power per frontal cross-sectional area) of constructive interference of N identical in-phase waves is higher than the intensity of the single wave by the factor $N^2$ as a superposition of waves results in the summing of wave's amplitudes and the intensity of wave (in particular, of the resulting wave), having the sense of the power of wave per a cross-sectional area, is proportional to the second power of the wave's amplitude; so, the inventor points out that the cumulative intensity of the N identical in-phase superposed waves is higher than the sum intensity of these waves, but yet to be superposed, by the factor N;

a well-known effect of a sound beam focusing, and, thereby, boosting a sound loudness;

a well-known waveguide effect observed as the transmission of a sound beam through a pipe; and a well-known effect of sound loudness boosting in a gramophone by using an exponentially-divergent horn.

For the purposes of the present patent application, the term "molecular fluid" should be understood as a fluid substance composed of randomly moving and interacting molecules, according to the kinetic theory of matter;

Referring to the defined term "molecular fluid", the term "flow velocity" is specified as a measure of the molecular fluid molecules motion in a prevalent direction in addition to the random Brownian movement;

the term "M-velocity" should be understood as a velocity measured in Mach numbers;

the term "specific M-velocity", indicated by $M_*$, is introduced. The value of the specific M-velocity $M_*$ is defined in prior arts A01, A02, and A03 as a dimensionless quantity equal to $\sqrt{(\gamma-1)/\gamma}$, where $\gamma$ is a compressibility parameter, in turn, determined by a specific molecular structure of fluid; for a hypothetically ideal gas, the compressibility parameter $\gamma$ becomes equal to adiabatic compressibility constant j, in turn, specified as equal to $1+2/f$, where f is the number of degrees of freedom per molecule of the hypothetical ideal gas; f depends on a configuration of molecules of the hypothetical ideal gas; for instance, for air having dominantly bi-atomic molecules, f=5 and j=7/5 are good approximations;

the term "heat-like energy of fluid" or "heat energy in a broad sense" should be understood in a wide sense including both:

the internal heat energy of fluid, i.e. the kinetic energy of the random Brownian motion of fluid molecules; and the kinetic energy of concomitant turbulence defined as random whirling of groups of molecules;

the term "convergent-divergent in a broad sense" applied to a nozzle should be understood as either converging, divergent, convergent-divergent, divergent-convergent, multi-stage (for instance, two-stage) convergent-divergent, piecewise-divergent, or piecewise-convergent-divergent; and the term "sound loudness booster" or "sound booster" or "sound-booster" should be understood as an amplifier of sound intensity.

Venturi Effect

Reference is now made to prior art FIG. 1b. FIG. 1b is a schematic illustration of an airfoil-shaped convergent-divergent nozzle 102, pipe-section in a sagittal plane. The shape can be described as comprising an inlet part 103 constricting into a narrow throat 104, further followed by a divergent outlet part 105. When a fluid 106 flows slowly through convergent-divergent nozzle 102, a jet-effect is observed in an adiabatic process, i.e. velocity increases in narrow throat 104 at the expense of the static pressure in fluid 106. Speedometers 1071, 1072, 1073 and barometers 1081, 1082, 1083 illustrate the interrelated behavior of the velocity and static pressure. This jet-effect is known also as the Venturi effect. Thus, the Venturi acceleration effect is observed in the case of a slow and converging flow, and the Venturi retarding-effect is observed in the case of slow and divergent flow.

The inventor points out and emphasizes that the phenomenon of the Venturi effect is the self-acceleration and self-retarding of an airflow portion, i.e. is the airflow velocity self-oscillation, at the expense of the air portion's warmth. I.e., in other words, the Venturi effect of the airflow velocity self-oscillation (as well as the Coanda-jet-effect) has the jet-effect nature.

De Laval Effect

Reference is now made to prior art FIGS. 1c and 1d. FIG. 1c shows schematically a pipe 100 referred to the de Laval nozzle that, in principle, is similar to pipe 102 shown in FIG. 1b, but now the incoming fluid-flow 101 is sufficiently fast such that fluid 101 becomes substantially compressible-expandable. In this case, in an adiabatic process, the de Laval effect is observed. This is the effect of the extension of fluid 101 in the divergent outlet part 142 resulting in a further decrease of the static pressure and temperature and a correlated increase of the flow velocity.

FIG. 1d illustrates schematically graphics of distributions of the fluid-flow 101's (FIG. 1c) three parameters: velocity 150, static pressure 160, and temperature 170, each along the length of nozzle 100. A standard rocket convergent-divergent jet-nozzle 100 can be modeled as a cylinder 140 that leads to a constriction 141, known as the "throat", which leads into a widening "exhaust bell" 142 open at the end. The location of the narrowest cross-section of the throat is called the "critical condition" point 180. High speed and therefore compressible-expandable hot fluid 101 flows through throat 141, where the velocity picks up 151 and the pressure and temperature fall, 161 and 171 correspondingly. Hot fluid 101 exits throat 141 and enters the widening exhaust bell 142. It expands rapidly, and this expansion drives the velocity up 152, while the pressure and temperature continue to fall, 162 and 172 correspondingly. This jet-effect phenomenon of fluid 101 extra-acceleration at the expense of the fluid 101 heat energy, defined by the static pressure, temperature, and density, is applied to jet-engines, particularly to accelerate a rocket. A sharp slope of the static pressure, observed in throat 141, results in pressure waves, called Mach waves. An undesired influence of the Mach waves in the de Laval nozzle is described, for example, in U.S. Pat. No. 8,611,787 "Rocket nozzles for unconventional vehicles" by Bulman.

Enhanced Venturi Effect and Enhanced de Laval Effect

In A01, A02, and A03, the enhanced implementations of jet-effects: the Venturi effect, the de Laval jet-effect, and the de Laval retarding-effect, are suggested, wherein the essence of the improvement is in stationary geometrical configurations of a nozzle, convergent-divergent in a broad sense, playing the role of a Venturi pipe and a de Laval jet-nozzle, correspondingly, such that the stationary geometrical configurations are passively adapted to a certain velocity and thermodynamic parameters of an incoming fluid flow to provide for laminar flow. Namely, the prior art improved passively adapted stationary geometrical configuration of a de Laval jet-nozzle is such that the varying convergent-divergent cross-sectional area is characterized by a passively adapted cross-sectional area profile function A(x) given by a reference equation expressed as:

$$A(x) = \frac{A_*}{M(x)} \left( \frac{\gamma-1}{\gamma} \right)^{\frac{1}{2}} \left( \frac{2+\gamma(M(x))^2}{\gamma+1} \right)^{\frac{\gamma+1}{2(\gamma-1)}}, \quad \text{Eq. (1.a)}$$

where $A_*$ is the minimal cross-sectional area of a narrow throat between the convergent and divergent portions of the de Laval jet-nozzle, $\gamma$ is an adiabatic compressibility parameter of the fluid flow, and M(x) is a gradually-smoothed monotonic function of x representing a profile of an M-velocity of the fluid flow moving within and through the nozzle. The reference equation Eq. (1.a) is derived from the equation of continuity:

$$A(x) \times \rho(x) \times u(x) = Const, , \quad \text{Eq. (1.b)}$$

where:
x is coordinate in the x-direction of the fluid flow headway motion,
A(x) is a cross-sectional area in the frontal plane at the x-coordinate,
$\rho(x)$ is the temperature-and-pressure-dependent mass density function of x, and
u(x) is x-component of headway velocity,
applied to a portion of the molecular fluid flow moving in the x-direction and being subjected to a cross-sectional area varying in an adiabatic process. Prior art FIGS. 1e and 1f, each of which having Scheme (A) and Graph (B), extracted from A03, illustrate optimized convergent-divergent nozzles characterized by cross-sectional area profile functions $A_{1e}$(x) and $A_{1f}$(x), correspondingly. In general, the cross-sectional area profile functions $A_{1e}$(x) and $A_{1f}$(x) are kids of A(x) expressed by the reference Eq. (1.a) specified by parameters $A_{*1e}$ and $A_{*1f}$ and by gradually-smoothed monotonic functions $M_{1e}$(x) and $M_{1f}$(x), correspondingly; wherein the cross-sectional area profile function $A_{1e}$(x) is specified to trigger the enhanced de Laval jet-effect to accelerate a relatively slow laminar flow and the cross-sectional area profile function $A_{1f}$(x) is specified to trigger the enhanced de Laval retarding-effect to decelerate a laminar flow. There are indications:

In prior art FIG. 1e:
Nozzle 610 has a through-hole tunnel, the shape of which is characterized by the cross-sectional area profile function $A_{1e}$(x);
Laminar flow 611 entering nozzle 610 with a certain M-velocity being lower than the specific M-velocity $M_*$ defined as equal to $\sqrt{(\gamma-1)/\gamma}$;
Converging inlet funnel 612;
Convergent-divergent portion 613, further specified as the portion between the cross-sections 6131 and 6132, having a narrow throat, the minimal cross-sectional area of which is in the frontal plane 618, called "a critical condition point", where the M-velocity of flow is equal to the specific M-velocity $M_*$;
Divergent exhaust tailpipe 614;
Sagittal axis 615;
Laminar outflow 616, outflowing from the divergent exhaust tailpipe 614 with a certain M-velocity higher than the specific M-velocity $M_*$; and
The distribution of the fluid's three parameters: velocity 620, static pressure 630, and temperature 640 along the length of nozzle 610, are performed as monotonic functions, wherein:
the velocity 620 is monotonically increasing 621 and 622 in both the converging stage of the nozzle 610 upstream before the critical condition point 618 and the divergent stage of the nozzle 610 downstream behind the critical condition point 618; the velocity 623 corresponds to the specific M-velocity $M_*$;
the static pressure 630 is monotonically decreasing 631 and 632 in both the converging stage of the nozzle 610 upstream before the critical condition point 618 and the divergent stage of the nozzle 610 downstream behind the critical condition point 618; and
the absolute temperature 640 is monotonically decreasing 641 and 642 in both the converging stage of the nozzle 610 upstream before the critical condition point 618 and the divergent stage of the nozzle 610 downstream behind the critical condition point 618;
and In prior art FIG. 1f:

Nozzle 650 has a through-hole tunnel shape of which is characterized by the cross-sectional area profile function $A_{1f}(x)$;

Laminar flow 651 entering nozzle 650 with a certain M-velocity being higher than the specific M-velocity $M_*$;

Converging inlet funnel 652;

Convergent-divergent portion 653, further specified as the portion between the cross-sections 6531 and 6532, having a narrow throat, the minimal cross-sectional area of which is in the frontal plane 658, called "a critical condition point", where the M-velocity of flow is equal to the specific M-velocity $M_*$;

Divergent exhaust tailpipe 654;

Sagittal axis 655;

Laminar outflow 656, outflowing from the divergent exhaust tailpipe 614 with a certain velocity lower than the specific M-velocity $M_*$; and The distribution of the fluid's three parameters: velocity 660, static pressure 670, and temperature 680 along the length of nozzle 650, are performed as monotonic functions, wherein:

the velocity 660 is monotonically decreasing 661 and 622 in both the converging stage of the nozzle 650 upstream before the critical condition point 658 and the divergent stage of the nozzle 650 downstream behind the critical condition point 658, correspondingly; the velocity 663 corresponds to the specific M-velocity $M_*$;

the static pressure 670 is monotonically increasing 671 and 672 in both the converging stage of the nozzle 650 upstream before the critical condition point 658 and the divergent stage of the nozzle 650 downstream behind the critical condition point 658; and the absolute temperature 660 is monotonically increasing 661 and 662 in both the converging stage of the nozzle 650 upstream before the critical condition point 658 and in the divergent stage of the nozzle 650 downstream behind the critical condition point 658;

Furthermore, one can concatenate a triplet of convergent-divergent cross-sectional area profile functions: $A_{1f}(x)$, $A_{CAVITY}(x)$, and $A_{1e}(x)$, to provide for a triplet of sequentially-cascaded enhanced jet-effects: the enhanced de Laval retarding-effect, the enhanced Venturi effect, and the enhanced de Laval jet-effect, correspondingly, and, thereby, to provide a two-stage de Laval effect action as shown in prior art FIG. 1g extracted from A03 as well, wherein there are indications as follows:

Nozzle 690 has the cross-sectional area profile function $A_{690}(x)$ composed of the concatenated convergent-divergent cross-sectional area profile functions $A_{1f}(x)$, $A_{CAVITY}(x)$, and $A_{1e}(x)$; wherein as a two-stage de Laval effect action is assumed, the nozzle 690 is also called "a two-stage convergent-divergent nozzle";

In the first stage, which is characterized by the convergent-divergent cross-sectional area profile function $A_{1f}(x)$, laminar flow 691:

enters the nozzle 690 with a certain M-velocity being higher than the specific M-velocity $M_*$;

is subjected to a gradual convergence within the converging inlet funnel 692; and becomes reshaped in the convergent-divergent portion 693 having a narrow throat, the minimal cross-sectional area of which is in the frontal plane 6981;

In wide cavity 694 which is characterized by the convergent-divergent (saying strictly, divergent-convergent) cross-sectional area profile function $A_{CAVITY}(x)$:

A wide front flow 695 moves with an M-velocity $M_{CAVITY}(x)$ lower than the specific M-velocity $M_*$ that provides for the flow 695 to be subjected to the enhanced Venturi effect within the wide cavity 694;

The primary requirement for the function $M_{CAVITY}(x)$ is to smooth jumps between the gradually-smoothed monotonic functions $M_{1f}(x)$ and $M_{1e}(x)$ to provide for that the unbroken function $M_{690}(x)$ composed of the concatenated gradually-smoothed monotonic functions $M_{1f}(x)$, $M_{CAVITY}(x)$, and $M_{1e}(x)$ remains a gradually-smoothed function of x representing a profile of an M-velocity along the nozzle 690's length;

and

The second stage, which is characterized by:

the convergent-divergent cross-sectional area profile function $A_{1e}(x)$;

Convergent-divergent portion 696 having a narrow throat, the minimal cross-sectional area of which is in the frontal plane 6982;

Divergent exhaust tailpipe 697; and

Laminar outflow 699, outflowing from the divergent exhaust tailpipe 697 with a certain velocity higher than the specific M-velocity $M_*$.

In this patent application:

On the one hand, a disclosed specific divergent portion of the cross-sectional area profile function A(x) is used to implement an enhanced horn which, when exposed to a sound, is capable of amplifying the sound loudness to play the role of an improved horn of a gramophone, a disclosed cascaded multiplicity of the enhanced horns, which as a whole can be used as an improved waveguide capable of conveying the sound and amplifying the sound loudness; the waveguide can be used as an improved waveguide-phonendoscope, and a disclosed concatenation of specific convergent-divergent portions of convergent-divergent cross-sectional area profile functions $A_1(x)$, $A_{CAVITY}(x)$, and $A_2(x)$ is used to implement a waveguide capable of conveying the sound and amplifying the sound loudness; the waveguide can be used as an improved phonendoscope, wherein both: the improved horn of gramophone and the improved phonendoscope, boost the sound loudness at the expense of concomitant turbulence accompanying the sound propagation and heat of the ambient fluid; and On the other hand, a disclosed specific convergent-divergent portion of the cross-sectional area profile function A(x) is used to implement an improved sound-silencer, and a disclosed cascaded multiplicity of the enhanced convergent-divergent nozzles, which as a whole can be used as an improved sound-silencer capable of dissipating the sound and thereby reducing the sound loudness; the improved sound can be used as an improved isolator of sound, wherein an efficient suppression of sound is a manifestation of the wave power transformation into the heat of the ambient fluid.

Sound as Complicated Movement in Molecular Fluid

In physics, an acoustic (elastic) wave (infrasound, audible sound, or ultrasound) is an oscillation accompanied by a transfer of energy that travels through a medium. Waves consist of oscillations or vibrations of particles (molecules), around almost fixed locations. For the purposes of the present patent application, the medium conveying the sound is fluid where the molecules have additional degrees of freedom of the Brownian motion and a motion in a prevalent direction.

A forcedly accelerated membrane is a trivial aerodynamic device—a fluid pusher-off, capable of originating an elastic wave propagating in the ambient fluid. Wave motion transfers energy from one point to another, displacing particles of the transmission medium with little or no associated mass transport. From the point of view of the energy consumption by a source of the acoustic wave, the energy transmission is given free of charge; it is given at the expense of the heat energy of the ambient fluid as a result of the triggered waving jet-effect as described in A02 and A03. The wavefront propagates in accordance with the Huygens-Fresnel principle saying that every point, which a wave-front disturbance reaches, becomes a source of a secondary spherical wave, wherein the interference superposition of these secondary waves determines the form of the wave at any subsequent time.

In physics, sound (acoustic wave) in a fluid is interpreted as an oscillating change of the fluid's thermodynamic parameters, namely, the oscillating change of the static pressure P, mass density $\rho$, and absolute temperature T, wherein the thermodynamic parameters are interrelated according to the van der Waals law of fluid state in an adiabatic process. In general, when a portion of the fluid is subjected to an adiabatic process, the adiabatic process in gas is described by the condition $P/\rho^\gamma$=Const or $P/T^{\gamma/(\gamma-1)}$=Const or the equivalent thermodynamic differential equations interrelating changes in absolute temperature T, mass density, and static pressure P of gas as follows:

$$\begin{cases} \dfrac{d\rho}{\rho} = \dfrac{1}{\gamma}\dfrac{dP}{P} & \text{Eq. (1.1a)} \\ \dfrac{dT}{T} = \dfrac{\gamma-1}{\gamma}\dfrac{dP}{P} & \text{Eq. (1.1b)} \end{cases}$$

Wherein, the oscillating changes in the fluid's thermodynamic parameters are such to result in triggering of the jet-effect manifested as fluid motion in the form of the propagating acoustic wave.

For the sake of concretization and without loss of generality, consider:
- the air as a particular case of the fluid, and
- the sound propagating in the air as a particular case of the acoustic wave propagating in the fluid.

The associated with sound oscillating changes of the fluid's thermodynamic parameters along an axis x collinear with the direction of the sound propagation is expressed as:

$$\begin{cases} \delta P = \Delta P \times e^{-i(\omega t - \kappa x)} & \text{Eq. (1.2a)} \\ \delta \rho = \Delta \rho \times e^{-i(\omega t - \kappa x)} & \text{Eq. (1.2b)} \\ \delta T = \Delta T \times e^{-i(\omega t - \kappa x)} & \text{Eq. (1.2c)} \end{cases}$$

where:
- $\delta P$, $\delta \rho$, $\delta T$ are the oscillating changes of the static pressure, the mass density, and the absolute temperature, correspondingly;
- $\Delta P$, $\Delta \rho$, $\Delta T$ are amplitudes of the oscillating change of the static pressure, the mass density, and the absolute temperature, correspondingly;
- $\omega$ is the cyclic frequency of the oscillating change;
- $\kappa$ is the wavenumber interrelated with the cyclic frequency $\omega$ of the acoustic wave as
    $\kappa = \omega/u_s$, where $u_s$ is the phase velocity of the sound propagation in the fluid.

Taking into account the interrelations between the thermodynamic parameters in an adiabatic process described by the equations Eqs. (1.1a) and (1.1b), the equations Eqs. (1.2a), (1.2b), and (1.2c) describing the oscillating changes of the fluid's thermodynamic parameters associated with the sound are rewritten as a system of equivalent equations as follows:

$$\begin{cases} \dfrac{\delta P}{P} = \dfrac{\Delta P}{P} \times \exp[-i(\omega t - \kappa x)] & \text{Eq. (1.3a)} \\ \dfrac{\delta \rho}{\rho} = \dfrac{1}{\gamma}\dfrac{\Delta P}{P} \times \exp[-i(\omega t - \kappa x)] & \text{Eq. (1.3b)} \\ \dfrac{\delta T}{T} = \dfrac{\gamma-1}{\gamma}\dfrac{\Delta P}{P} \times \exp[-i(\omega t - \kappa x)] & \text{Eq. (1.3c)} \end{cases}$$

A human-hearer perceives the oscillating changes of the air static pressure as sound loudness; the air static pressure, absolute temperature, and mass density are measured by the so-called "SPL" (sound pressure level), "STL" (sound temperature level), and "SDL" (sound density level), correspondingly; and the sound loudness is measured also by "SIL" (sound intensity level) or "SWL" sound power level.

The SPL is measured in decibels (dB). It is equal to $20\times\log_{10}$ of the ratio of the route mean square (RMS) of sound pressure to the reference of sound pressure that (the reference sound pressure) in the air is $2\times10^{-5}$ N/m$^2$ or 0.0002 Pa, in turn, corresponding to the reference acoustic wave power (the loudness as power) estimated approximately as $10^{-12}$ W. The characteristic SPL of speakers is defined for a distance of 1 m from the speaker. Normally, a range of the characteristic SPL for a speaker is between 0 to 80 dB that corresponds to changes in the static pressure in the range from 0.0002 Pa to 2 Pa and changes in the acoustic wave power in the range from $10^{-12}$ W to $10^{-4}$ W. Using the equation Eq. (1.3c), the reference sound temperature in the air is estimated as $5.4\times10^{-10}$K and the range of temperature changes for the speaker is estimated from $5.4\times10^{-10}$K to $5.4\times10^{-6}$K.

Sound (acoustic wave) is considered as a complicated movement of a molecular fluid, wherein the complicated movement is composed of:

- The Brownian motion of the air molecules with the Brownian velocity, indicated by $u_{Brownian}$, which interrelates with the velocity of sound $u_{sound}$ as $u_{Brownian} = \sqrt{3/\gamma} \times u_{sound}$; $u_{sound} \approx 345$ m/sec and $u_{Brownian} \approx 500$ m/sec.
- The oscillating motion of molecules with so-called "particle velocity", the amplitude of which is indicated by $u_{particle}$ and interrelated with the sound loudness; normally, in the air,
    near an oscillating membrane which is a source of the sound, the particle velocity amplitude $u_{particle}$ is predetermined by the velocity of the oscillating membrane and is between 0.1 m/sec and 10 m/sec, while far from the oscillating membrane, where the sound front becomes substantially widened, the particle velocity amplitude $u_{particle}$ is very low: between $5 \times 10^{-8}$ m/sec and $5 \times 10^{-4}$ m/sec;

wherein the particle velocity relates to the mass of the oscillating air as a whole; note that, considering a local slow flow moving with the particle velocity, a widening of a frontal cross-sectional area is accompanied by a decrease in the amplitude of the particle velocity, according to the equation of continuity;

The specific conveying motion that is interrelated with the cascaded oscillating motion of particles moving with the "particle velocity" that [the "particle velocity"], in turn, is interrelated with the acoustic wave amplitude manifested as the sound loudness. The specific conveying motion is a kind of movement, which (in contrast to the oscillating motion of the air as a whole) is interpreted as a directional motion of a tiny portion of fluid mass that [the tiny portion of mass] determines the air mass density oscillating change only. The specific conveying motion can be interpreted as composed of two complementary alternating movements of positive and negative changes in air mass density, wherein both alternating movements are in the same direction (that is the direction of sound propagation) and, when in open space, with the M-velocity of 1 Mach. The so-called Umov-vector is a measure of the specific conveying motion of the tiny portion of the fluid mass. The SPL, characterizing the sound loudness, is interrelated with the so-called: "SVL" (sound particle velocity level). Thus, the oscillating (positive and negative) change in mass density along the direction of the wave propagation (again, which is interrelated with the sound loudness) is considered as the directional motion of the tiny mass, wherein the motion is with the mass density change conveying velocity $u_{convey}$ that is the same as the velocity of sound $u_{sound}$, i.e., when propagating in open space, M-velocity of 1 Mach; and The concomitant turbulent motion, as dis-laminarity of the mentioned oscillating and conveying components of the complicated movement of air, depends on both the shape of an acoustic waveguide (for instance, a horn) and the acoustic wave amplitude (sound loudness);

wherein, in contrast to acoustic waves in open space where the turbulent component of fluid motion, inherently-accompanying the acoustic waves, causes the inevitable dissipation of the propagating acoustic waves manifested as a decrease of sound loudness, the turbulent component of fluid motion within an acoustic waveguide is pre-determined by restricted degrees of freedom, so, the acoustic waveguide, if elaborated, can provide for reduced concomitant turbulence accompanied by increased intensity of sound. In other words, the elaborated acoustic waveguide plays the role of a fluid pusher-off capable of transforming the kinetic power of the concomitant turbulence into the wave power accompanied by increased both the particle velocity amplitude $u_{particle}$ and the conveying velocity $u_{convey}$.

When a sound is originated by an oscillating membrane of a classic source of acoustic waves rated by a power supplier, the net-efficiency, defined for the classic source of acoustic waves as the ratio of the power of sound to the supplied power, normally, is between 0.1% and 2%. The mentioned originated concomitant turbulence, originated due to sudden jumping changes of thermodynamic parameters and velocity of adjacent fluid portions, especially, near the edges of the moving membrane, is the dominant reason for:

such a low net-efficiency of sound launching and, vice-versa, detection (the introduced term "sound detection" should be understood as registration and/or recording the electric voltage and/or current induced in the electrical circuit due to sound impact); and that, when the sound is propagating in open space, the sound loudness measured in SPL is further decreasing exponentially with the propagation path increase; wherein the exponential decrease in SPL is stronger for the sound of higher frequencies.

I.e., in other words, 98% to 99.9% of the power consumed by a classic source of acoustic waves goes for the kinetic power of the undesired turbulent motion of the ambient fluid.

One way to reduce the undesired concomitant turbulence accompanying the originated sound is to reduce the ratio of the amplitude of motion to the area of an oscillating membrane and, thereby, to reduce the contribution of the sudden jumping changes of thermodynamic parameters and velocity of adjacent fluid portions to the concomitant turbulence. For example, it is the commonly used piezo-effect manifested as small deformations of a piezo plate originating an ultrasound. However, taking into account that the power of sound is proportional to squared both amplitude and frequency of oscillation, the way can provide for the audible sound of unpractically ultra-low power and has a practical sense to launch and detect the ultrasound only.

There is, therefore, a need in the art for a method and apparatus to provide an improved design of a source and detector of acoustic waves; wherein, in particular, a net-efficiency would be increased by suppression of originated concomitant turbulence in the ambient fluid.

Horn as Sound-Booster

In nature, male mole crickets amplify their song using a specifically built burrow having a shape of a coupled horn; wherein its 3.5 milliwatts of mechanical power results in a sound that can be heard up to 600 (six hundred) meters away; as well, cracker butterflies (Hamadryas) amplify their "cracking" sound using much more miniature horns formed by their veins; wherein thereby boosted sound becomes audible for humans from 30 meters.

In industry, to reduce the kinetic power of the concomitant turbulence and thereby to increase the net-efficiency of sound launching, one uses an elaborated nozzle as an aerodynamic apparatus capable of transforming the kinetic energy, in general, of fluid particles, and, in particular, of the concomitant turbulence into the wave power of the sound. When a gramophone is supplied with an exponentially-divergent horn, the effect of sound boosting is well-known.

FIG. 1n, a prior art illustration of horns playing the role of a sound loudness booster, is divided into three schematic drawings: case (A), case (B), and case (C) as follows:

Case (A), illustrating a megaphone-A 1n.A comprising a movable membrane 1n.A1, capable of a controlled oscillating motion originating a sound, and an exponentially-divergent horn 1n.A2 having an outlet area 1n.AA;

Case (B), illustrating a megaphone-B 1n.B comprising a movable membrane 1n.B1, capable of a controlled oscillating motion originating a sound, and a triple-folded exponentially-divergent horn formed by three cascaded sequentially scaled parts: 1n.B2, 1n.B3, and 1n.B4. The triple-folded exponentially-divergent horn as a whole has an outlet area 1n.BA which is the same as the outlet area 1n.AA; in another view, megaphone-B 1n.B differs from megaphone-A 1n.A by the triple-folded cumulative length of the exponentially-divergent nozzle. It is found that, while megaphone-A 1n.A increases the intensity of the originated sound on 10 dB, the megaphone-B 1n.B increases the intensity of the originated sound on 20 dB; and Case (C), illustrating a gramophone 1n.C supplied by an exponentially-divergent nozzle 1n.C1 playing the role of the acoustic waveguide. Diameter $D_{ou}$ 1n.C2 of sound-outlet of the exponentially-divergent nozzle 1n.C1 is greater than the diameter $D_{in}$ of a narrow sound-inlet throat 1n.C3 by the factor $F_D$ that is much greater than 1, in some implementation, the factor $F_D$ is equal to 60. The factor $F_D$ equal to 60 corresponds to the area-variation ratio of the sound frontal-outlet cross-sectional area to the sound frontal-inlet cross-sectional area of 3,600. The exponentially-divergent nozzle 1n.C1 is destined to solve the problem to widen the frontal cross-sectional area of sound rather than to contribute, in general, to the heat in a broad sense, and, in particular, to the concomitant turbulence of moving fluid. When a sound is established, in addition to the mentioned complicated movement of fluid, a portion of air, that takes a place within the exponentially-divergent nozzle 1n.C1, is subjected to forward-and-backward oscillating longitudinal motion accompanied by substantial deformations and accelerations of the air portion. If to ignore the de Laval jet-effect, it is expected that the area-variation ratio of 3,600 is accompanied by the air velocity inverse ratio of the same order of value. When considering the fluid motion component moving with the conveying velocity $u_{convey}$, a change in cross-sectional area of longitudinally-moving change in fluid mass density triggers the de Laval jet-effect, as soon as the velocity $u_{convey}$ measured in Mach numbers is higher than the specific M-velocity, and, when considering the fluid motion component moving with the particle velocity $u_{particle}$, a local change in the cross-sectional area of forward-and-backward oscillating longitudinally moving fluid triggers the local Venturi effect. In any case for an elaborated horn, the jet-effect of a transformation of both:
the fluid heat energy, and
the energy of the concomitant turbulence,
into the energy of the fluid oscillating motion is manifested as sound loudness boosting.

It is also commonly known that:
when a waveguide of a certain length is used for conveying a sound, the effect of resonance of the sound of a certain frequency within the waveguide is observed; and
a horn as a musical instrument in which sound is produced by the vibration of air, typically by the player blowing into the instrument, is characterized by a specific timbre dependent on the horn's geometrical configuration.

Sometimes, when conveying a sound through an acoustic waveguide, a distortion of the frequency spectrum of the original sound and, in particular, the effect of resonance are unwanted.

External Ear

FIG. 1L comprises a schematic drawing of a sectional profile of a human ear in a sagittal plane. External ear 1L.0 of human comprises a pinna and ear canal. The pinna, destined to be exposed to an incoming sound, comprises a funnel characterized by an outer-inlet cross-section 1L.1. The ear canal, destined for conveying the sound to eardrum 1L.6, comprises an ear canal inlet cross-section 1L.2 such that the pinna funnel outer-inlet cross-sectional area is greater than the ear canal inlet cross-sectional area by the factor $F_{12}$ of, approximately, 5.5. The ear canal is a tunnel for sound, further characterized by:

an after-inlet widened cross-section 1L.3, the cross-sectional area of that is greater than the cross-sectional area of the ear canal inlet cross-section 1L.2 by the factor $F_{32}$ of at least 1.1, a narrow throat cross-section 1L.4, the cross-sectional area of that is smaller than the cross-sectional area of the ear canal after-inlet widened cross-section 1L.3 by the factor $F_{34}$ of, approximately, 3; moreover, the cross-sectional area of the ear canal inlet cross-section 1L.2 is greater than the cross-sectional area of the narrow throat cross-section 1L.4 by the factor $F_{14}$ of approximately 2.7; and a wide outlet cross-section 1L.5 adjacent to the eardrum 1L.6, the cross-sectional area of that [1L.5 or 1L.6] is greater than the cross-sectional area of the ear canal narrow throat cross-section 1L.4 by the factor $F_{54}$ of, approximately, 5.5.

There is, therefore, a need in the art for a method and apparatus to provide proper analysis and optimal design of a divergent horn and two-stage convergent-divergent nozzle to implement applications appropriate for use in industry for efficient amplifying of acoustic waves intensity based on effects of sound loudness boosting within a shaped channel.

SUMMARY OF THE INVENTION

Unity and Novelty of the Invention

The unity and novelty of the invention are in a method providing for the use of a specifically shaped convergent-divergent jet-nozzle, convergent-divergent in a broad sense, applied to an acoustic waveguide to provide for:
reducing a turbulent component of fluid motion inherently-accompanying acoustic waves and inevitably-causing dissipation of a propagating sound;
amplifying the intensity of acoustic waves at the expense of both the heat energy and the concomitant turbulence of moving fluid and so to boost the loudness of sound; or, contrariwise,
transforming the wave power of elastic waves into the heat of the ambient fluid.

Primary Basic Features of the Present Invention

The claims define the invention.

One of the primary features of the present invention is a broken or solid geometrical configuration of a through-hole tunnel-waveguide between an open sound-inlet and an open sound-outlet; the through-hole tunnel-waveguide is submerged in fluid and exposed to entering sound propagating in the fluid; the sound is considered as a complicated motion in a molecular fluid comprising a motion of a tiny portion of the fluid, wherein the tiny portion of the fluid is defined as characterizing the fluid density change associated with the propagating sound and is moving within and through the through-hole tunnel-waveguide; the through-hole tunnel-waveguide is destined to play the role of:
a sound-booster, to:
solve the problem of the sound power dissipation into the heat energy of fluid,
convey the sound from the sound-inlet to the sound-outlet, and amplify the sound loudness at the expense of both the heat energy and concomitant turbulence of the moving fluid;

or, contrariwise, a sound-silencer, to suppress a waveguide effect and transform the acoustic wave power into the ambient heat thereby solving the problem of sound propagation.

The geometrical configuration of the through-hole tunnel-waveguide, functioning as the sound-booster or, contrary-wise, sound-silencer, is generally recognized by a convergent-divergent profile, convergent-divergent in a broad sense, i.e. the through-hole tunnel-waveguide is either: a divergent horn, or convergent-divergent pipe, or two-stage convergent-divergent nozzle, or piecewise-divergent pipe, or piecewise-convergent-divergent pipe, the sound-inlet of which is exposed to entering sound; and is specifically recognized by a varying cross-sectional area characterized by a cross-sectional area profile function A(x), either continuously-smooth or piecewise-broken-with-intervals piecewise-smooth, which:

in the case of the solid divergent horn playing the role of the sound-booster and when the sound-inlet has a cross-sectional area $A_{IN}$, the cross-sectional area profile A(x) is a divergent cross-sectional area profile function $A_{HORN}(x)$ expressed as:

$$A_{HORN}(x) = \frac{A_{IN}}{M_{HORN}(x)} \left( \frac{2 + \gamma(M_{HORN}(x))^2}{2 + \gamma} \right)^{\frac{\gamma+1}{2(\gamma-1)}}, x_a < x < x_b,$$

where $\gamma$ is an adiabatic compressibility parameter of the fluid, $x_a$ and $x_b$ are x-coordinates of the open sound-inlet and open sound-outlet, correspondingly, and $M_{HORN}(x)$ is a monotonically-increasing gradually-smooth function of x representing an M-velocity profile of the fluid tiny portion moving within and through the divergent horn;

in the case of the in-line arranged brokenly-cascaded array of N relatively-short and slightly-divergent horns considered as a whole playing the role of a waveguiding sound-booster and when each n-th of the N relatively-short and slightly-divergent horns (n=1, 2, ..., N) comprises a sound-inlet having a cross-sectional area $A_{IN,n}$, the cross-sectional area profile A(x) is a piecewise-broken-with-intervals piecewise-divergent cross-sectional area profile function $A_{BROKEN}(x)$ comprising slightly-divergent portions $A_n(x)$ each of which expressed as:

$$A_n(x) = \frac{A_{IN,n}}{M_n(x)} \left( \frac{2 + \gamma(M_n(x))^2}{2 + \gamma} \right)^{\frac{\gamma+1}{2(\gamma-1)}} \quad \begin{array}{l} x_{a,n} < x < x_{b,n} \\ n = 1, 2, \ldots, N \end{array}$$

where $\gamma$ is an adiabatic compressibility parameter of the fluid, where $x_{a,n}$ and $x_{b,n}$ are x-coordinates of the open sound-inlet and open sound-outlet, correspondingly, of the n-th divergent horn, and $M_n(x)$ is an n-th monotonically-increasing gradually-smooth function of x representing an M-velocity profile of the fluid tiny portion moving within and through the n-th slightly-divergent horn;

in the case of the convergent-divergent pipe playing the role of the sound-silencer and when the sound-inlet has a cross-sectional area $A_{IN}$ and the open sound-outlet has a cross-sectional area $A_{OU}$, the cross-sectional area profile $A_{PIPE}(x)$ is expressed as:

$$A_{SILENCER}(x) = \frac{A_{*SILENCER}}{M_{SILENCER}(x)} \left( \frac{\gamma - 1}{\gamma} \right)^{\frac{1}{2}} \left( \frac{2 + \gamma(M_{SILENCER}(x))^2}{\gamma + 1} \right)^{\frac{\gamma+1}{2(\gamma-1)}},$$

$$x_a < x < x_b$$

where $\gamma$ is adiabatic compressibility parameter of the fluid, $x_a$ and $x_b$ are x-coordinates of the open sound-inlet and open sound-outlet, correspondingly, $M_{SILENCER}(x)$ is a monotonically-decreasing gradually-smooth function of x representing an M-velocity profile of the fluid tiny portion moving within and through the convergent-divergent pipe, and $A_{*SILENCER}$ is a constant, being lesser than both the cross-sectional area of the pipe's sound-inlet $A_{IN}$ and the cross-sectional area of the pipe's open sound-outlet $A_{OU}$ and having the sense of the minimal cross-sectional area of a narrow throat between the converging and divergent parts of the convergent-divergent pipe, wherein the optimal ratio of the cross-sectional area of the pipe's sound-inlet $A_{IN}$ to the constant $A_{*SILENCER}$ is equal to $$\sqrt{\left(\frac{\gamma-1}{\gamma}\right)\left(\frac{2+\gamma}{\gamma+1}\right)^{\frac{\gamma+1}{(\gamma-1)}}},$$

in the case of the in-line arranged brokenly-cascaded array of N relatively-short convergent-divergent pipes considered as a whole playing the role of the sound-silencer and when each n-th of the N relatively-short convergent-divergent pipes (n=1, 2, ..., N) comprises a sound-inlet having a cross-sectional area $A_{IN,n}$ and a sound-outlet having a cross-sectional area $A_{OU,n}$, the cross-sectional area profile A(x) is a piecewise-broken-with-intervals piecewise-convergent-divergent cross-sectional area profile function $A_{BROKEN}(x)$ comprising convergent-divergent portions $A_n(x)$ each of which expressed as:

$$A_n(x) = \frac{A_{*n}}{M_n(x)} \left( \frac{\gamma - 1}{\gamma} \right)^{\frac{1}{2}} \left( \frac{2 + \gamma(M_n(x))^2}{\gamma + 1} \right)^{\frac{\gamma+1}{2(\gamma-1)}} \quad \begin{array}{l} x_{a,n} < x < x_{b,n} \\ n = 1, 2, \ldots, N \end{array}$$

where $\gamma$ is an adiabatic compressibility parameter of the fluid, $x_{a,n}$ and $x_{b,n}$ are x-coordinates of the open sound-inlet and open sound-outlet, correspondingly, of the n-th divergent horn, $M_n(x)$ is an n-th monotonically-decreasing gradually-smooth function of x representing an M-velocity profile of the fluid tiny portion moving within and through the n-th convergent-divergent pipe, and $A_{*n}$ is an n-th constant, being lesser than both the cross-sectional area of the n-th pipe's sound-inlet $A_{IN,n}$ and the cross-sectional area of the n-th pipe's open sound-outlet $A_{OU,n}$ and having the sense of the minimal cross-sectional area of a narrow throat between the converging and divergent parts of the n-th convergent-divergent pipe, wherein the constant $A_{*n}$ is lesser than both the n-th cross-sectional area of the pipe's sound-inlet $A_{IN,n}$ and the n-th cross-sectional area of the pipe's open sound-outlet $A_{OU,n}$, wherein the optimal ratio of the cross-sectional area of the n-th pipe's sound-inlet $A_{IN,n}$ to the constant $A_{*n}$ is equal to $$\frac{A_{IN,n}}{A_{*n}} = \sqrt{\left(\frac{\gamma-1}{\gamma}\right)\left(\frac{2+\gamma}{\gamma+1}\right)^{\frac{\gamma+1}{(\gamma-1)}}};$$

and in the case of the two-stage convergent-divergent nozzle playing the role of the sound-booster to be used as a phonendoscope, an inner canal is configured as a two-stage convergent-divergent tunnel comprising three sequentially joint fragments as follows:

A first convergent-divergent fragment;
A divergent-convergent cavity; and
A second convergent-divergent fragment;

wherein:

said open sound-inlet having the sound-inlet cross-sectional area, indicated by $A_{IN}$, is an open sound-inlet of the first convergent-divergent fragment, said open sound-outlet having the sound-inlet cross-sectional area, indicated by $A_{OU}$, is an open sound-outlet of the second convergent-divergent fragment, and the divergent-convergent cavity has a local maximal cross-sectional area, indicated by $A_{CA}$;

the cross-sectional area profile smooth function $A(x)$ is composed of sequentially concatenated cross-sectional area profile functions $A_1(x)$, $A_{CA}(x)$, and $A_2(x)$, wherein:

$A_1(x)$ is cross-sectional area profile function of the first convergent-divergent fragment, which provides for the enhanced de Laval retarding-effect resulting in deceleration of the fluid tiny portion, $A_2(x)$ is cross-sectional area profile function of the second convergent-divergent fragment, which provides for the enhanced de Laval jet-effect resulting in acceleration of the fluid tiny portion, and the cross-sectional area profile functions $A_1(x)$ and $A_2(x)$ are given by the equations expressed as:

$$\begin{cases} A_1(x) = \frac{A_{TH1}}{M_1(x)}\left(\frac{\gamma-1}{\gamma}\right)^{\frac{1}{2}}\left(\frac{2+\gamma(M_1(x))^2}{\gamma+1}\right)^{\frac{\gamma+1}{2(\gamma-1)}}, & x_{a,1} < x < x_{b,1} \\ A_2(x) = \frac{A_{TH2}}{M_2(x)}\left(\frac{\gamma-1}{\gamma}\right)^{\frac{1}{2}}\left(\frac{2+\gamma(M_2(x))^2}{\gamma+1}\right)^{\frac{\gamma+1}{2(\gamma-1)}}, & x_{a,2} < x < x_{b,2} \end{cases}$$

where:

$x_{a,1}$ and $x_{b,1}$ are x-coordinates of the open sound-inlet and open sound-outlet, correspondingly, of the first convergent-divergent fragment, $x_{a,2}$ and $x_{b,2}$ are x-coordinates of the open sound-inlet and open sound-outlet, correspondingly, of the second convergent-divergent fragment, $M_1(x)$ is a monotonically-decreasing gradually-smooth function of x, $M_2(x)$ is a monotonically-increasing gradually-smooth function of x, and $A_{TH1}$ and $A_{TH2}$ are local minimal cross-sectional areas of narrow throats of the first and second convergent-divergent fragments, correspondingly;

$A_{CA}(x)$ is cross-sectional area profile function of the divergent-convergent cavity defined between $x_{b,1}$ and $x_{a,2}$ such that providing for the enhanced Venturi effect as a gradually-smooth function $M_{CA}(x)$ of x, representing an M-velocity profile of the tiny portion of the fluid moving in the divergent-convergent cavity between the first and second narrow throats, remains lower than the specific M-velocity $M_* = \sqrt{(\gamma-1)/\gamma}$;

$M_1(x)$, $M_{CA}(x)$, and $M_2(x)$ are sequentially-concatenated to form a gradually-smooth function $M(x)$ of x, representing an M-velocity profile of the fluid tiny portion moving within and through the two-stage convergent-divergent nozzle's through-hole tunnel-waveguide; and interrelations between the cross-sectional areas $A_{IN}$, $A_{TH1}$, $A_{CA}$, $A_{TH2}$ and $A_{OU}$ satisfying conditions as follows:

$$\frac{A_{IN}}{A_{TH1}} \geq \sqrt{\left(\frac{\gamma-1}{\gamma}\right)\left(\frac{2+\gamma}{\gamma+1}\right)^{\frac{\gamma+1}{(\gamma-1)}}}, \quad (a)$$

$$A_{CA} > A_{TH1}, \quad (b)$$

$$A_{CA} > A_{TH2}, \quad (c)$$

$$A_{TH1} \geq A_{TH2}, \text{ and} \quad (d)$$

$$\frac{A_{OU}}{A_{TH2}} > \sqrt{\left(\frac{\gamma-1}{\gamma}\right)\left(\frac{2+\gamma}{\gamma+1}\right)^{\frac{\gamma+1}{(\gamma-1)}}}; \quad (e)$$

thereby providing for that, a portion of the propagating sound, entering the open sound-inlet, propagating through the two-stage convergent-divergent tunnel, and becoming launched from the open sound-outlet, becomes characterized by an amplified loudness.

Principal Objects

Accordingly, it is a principal object of the present invention to overcome the limitations of existing methods and apparatuses for efficient transformation of sound power, wherein the primarily disclosed apparatuses are sound transformers, on the one hand, either a horn of gramophone or a phonendoscope, both boosting the sound loudness, and, on the other hand, a convergent-divergent pipe suppressing the waveguide effect and thereby transforming the wave power into the ambient heat.

BRIEF DESCRIPTION OF THE DRAWINGS

To understand the invention and to see how it may be carried out in practice, a preferred embodiment will now be described, by way of a non-limiting example only, with reference to the accompanying drawings, in the drawings:

FIG. 1b is a prior art schematic drawing of the convergent-divergent Venturi tube;

FIG. 1c is a prior art schematic view of the convergent-divergent de Laval nozzle;

FIG. 1d is a prior art schematic illustration graphics of gas velocity, static pressure, and temperature distributions within the de Laval convergent-divergent jet-nozzle;

FIG. 1e is a prior art schematic illustration of an optimized convergent-divergent jet-nozzle;

FIG. 1f is a prior art schematic illustration of an optimized inverse convergent-divergent jet-nozzle;

FIG. 1g is a prior art schematic illustration of a two-stage convergent-divergent jet-nozzle, constructed according to the principles of the present invention;

FIG. 1n, composed of three parts: case (A), case (B), and case (C), comprises prior art schematic drawings of megaphones and a gramophone, each supplied by a horn;

FIG. 1L is a prior art schematic drawing of the external ear;

FIG. 2, composed of four parts: Case (A), Case (Cascade), Case (B), and Case (C), comprises schematic illustrations of sound boosters where: Case (A) is a horn for a gramophone, Case (Cascade) is a brokenly-cascaded waveguiding sound-booster, Case (B) is a phonendoscope, and Case (C) is a sound booster ergonomically adapted to a human's ear canal;

FIG. 3, composed of two parts: Case (A) and Case (B), comprises schematic illustrations of sound suppressers where: Case (A) is a sound-silencer and case (B) is a brokenly-cascaded in-line arranged sound-silencers of equal inlet and outlet cross-sectional areas.

All the above and other characteristics and advantages of the invention will be further understood through the following illustrative and non-limitative description of preferred embodiments thereof.

DETAILED DESCRIPTION OF PREFERRED EMBODIMENTS

The principles and operation of a method and an apparatus according to the present invention may be better understood with reference to the drawings and the accompanying description, it being understood that these drawings are given for illustrative purposes only and are not meant to be limiting. The DETAILED DESCRIPTION OF THE PREFERRED EMBODIMENTS is divided into two paragraphs: "Conceptual Idea" and "Embodiments", each having sub-paragraphs.

Conceptual Idea

Preface And Prerequisites

The inventor points out the facts that:
sound, as a complicated motion of fluid, comprises a headway conveying motion of a tiny portion of fluid characterizing moving changes in mass density which is associated with the sound loudness, wherein the density changes move with the conveying velocity $u_{convey}$ that is the same as the velocity of sound $u_{sound}$ in the fluid, i.e. the density changes move with a high M-velocity higher than the specific M-velocity $M_* = \sqrt{(\gamma-1)/\gamma}$. If so, when the sound propagates within a shaped tunnel, the conveying component of the complicated motion of sound is subjected to the de Laval effect. On the other hand, as described hereinabove in THE BACKGROUND OF THE INVENTION referring to prior art FIGS. 1e, 1f, and 1g, the de Laval effect can be optimized to become enhanced by suppression of turbulences and Mach waves origination and providing for an acceleration of a fluid flow at the expense of the fluid heat in the wide sense (i.e. including both the warmth and the energy of concomitant turbulence);

Considering the sound entering into and propagating within the exponentially-divergent horn 1n.C1 of gramophone 1n.C (prior art FIG. 1n), the headway conveying motion of the fluid tiny portion is such that the fluid tiny portion has the conveying M-velocity of 1 Mach at the entrance and further it is subjected to the exponential divergence but not to an optimized divergence which would be happened if the fluid tiny portion was leaking within the divergent exhaust tailpipe 614 of the convergent-divergent nozzle 610 (prior art FIG. 1e), thereby, the primary functionality of the used exponentially-divergent nozzle 1n.C1 can be improved if to use a specifically chosen portion of the convergent-divergent nozzle 610 shown in prior art FIG. 1f to accelerate the conveying component of the complicated motion of sound; and Considering the sound entering into and propagating within the external ear 1L.0 (prior art FIG. 1L):
on the one hand, the primary set of conditions satisfied for the shape of external ear 1L.1 is as follows:
the factor $F_{12} \approx 5.5$ is much greater than the ratio of 1 Mach to the specific M-velocity, i.e. $F_{12} > 1/M_*$,
$F_{32} > 1$,
$F_{34} > F_{32}$,
$F_{14} > 1$, and
$F_{54} > 1/M_*$;
and
on the other hand, the set of conditions can be satisfied when implementing a nozzle, which is similar to the two-stage convergent-divergent nozzle 690 shown in prior art FIG. 1g but further configured to satisfy the mentioned set of conditions as well as further restricting conditions providing for a laminar motion of the conveying component of the complicated motion of sound.

Thereby,

On the one hand, the external ear, as shaped to provide the mentioned set of satisfied conditions, when considered as a two-stage convergent-divergent nozzle applied to the conveying component of the complicated motion of sound, functions as a nozzle capable of two-stage de Laval effect action to accelerate the conveying component of complicated motion of fluid sound, and On the other hand, an elaborated two-stage convergent-divergent nozzle can be optimized to provide both laminarity and acceleration of the conveying component of the complicated motion of sound, wherein, when the accelerated conveying component of the complicated motion of sound becomes a motion in open space out of the nozzle, it reverts to the conveying motion with the velocity of sound in the open space thereby transforming the acquired kinetic energy of headway motion into the energy of sound characterized by increased amplitude of mass density oscillations, in turn, manifested as sound loudness boosting.

Essence of Concept: Use of Optimal Convergent-Divergent Jet-Nozzle

The primary idea of the present invention is to adapt the enhanced de Laval effect either for sound loudness boosting or, vice-versa, for suppression of sound loudness. Namely, the adaptation is such that either:

an optimized either divergent or two-stage convergent-divergent acoustic nozzle would play the role of an enhanced acoustic waveguide capable of:
  reducing a turbulent component of fluid motion accompanying the acoustic waves and causing dissipation of a propagating sound; and
  amplifying the intensity of acoustic waves at the expense of both the heat energy and the turbulence of fluid and so to boost the loudness of sound; or, alternatively, an optimized convergent-divergent acoustic nozzle would play the role of an enhanced sound-silencer capable of suppressing a waveguide-effect manifested as dissipating the wave power of propagating acoustic waves into the fluid heat.

EMBODIMENTS

FIG. 2, composed of four parts: Case (A), Case (Cascade), Case (B), and Case (C), illustrates modifications of a passive device having no moving parts designed in accordance with the principles of the present invention for boosting the sound loudness.

Optimized Horn for Gramophone

FIG. 2 Case (A) shows schematically an acoustic nozzle 2.A embodied as a divergent horn comprising a shaped through-hole tunnel having a divergent sectional profile. The divergent horn 2.A, the geometrical configuration of which is designed in accordance with principles of the present invention, is submerged in a molecular fluid (for the sake of concretization and without loss of generality, the molecular fluid is air) and exposed to a portion of sound 2.A0 launched by a source of acoustic waves 2.A10. The portion of sound 2.A0:

enters an open sound-inlet 2.A1 having a cross-sectional area $A_{IN}$, propagates within the divergent horn 2.A, reaches the open sound-outlet 2.A2 having a cross-sectional area $A_{OU}$, becomes launched from the open sound-outlet 2.A2, where, in the open space, is detected by a set of detectors 2.A30 of acoustic waves.

The specific conveying motion of the air density is interpreted as composed of two complementary alternating headway movements of positive and negative changes in air density, wherein both alternating headway movements are in the same direction (that is the direction of sound propagation) and, when the headway movements are in the open space, with the M-velocity of 1 Mach. When the sound portion 2.A0 propagates within the divergent horn 2.A, the specific conveying motion of the fluid tiny portion associated with the sound is subjected to the influence of bordering walls of the shaped through-hole tunnel 2.A.

The cross-sectional area of the shaped through-hole tunnel 2.A varies along the divergent horn 2.A's length in accordance with the equation Eq. (1.a) wherein there is taken into account the specific boundary condition at the sound-inlet where the M-velocity of the mentioned fluid tiny portion must be equal to 1 Mach. Thus, to provide for that the divergent horn 3.A functions as an enhanced sound-booster, the geometrical configuration of the shaped through-hole tunnel 2.A is characterized by a varying cross-sectional area profile function $A_{HORN}(x)$ of x-coordinates defined as increasing in a direction of sound propagation, wherein $A_{HORN}(x)$ is expressed as follows:

$$A_{HORN}(x) = \frac{A_{IN}}{M_{HORN}(x)} \left( \frac{2 + \gamma (M_{HORN}(x))^2}{2 + \gamma} \right)^{\frac{\gamma+1}{2(\gamma-1)}}, x_a < x < x_b, \quad \text{Eq. (2.1)}$$

where $\gamma$ is an adiabatic compressibility parameter of the fluid, $x_a$ and $x_b$ are x-coordinates of the open sound-inlet 2.A1 and open sound-outlet 2.A2, correspondingly, and $M_{HORN}(x)$ is a monotonically-increasing gradually-smooth function of x representing an M-velocity profile of the fluid tiny portion moving within and through the divergent horn 2.A.

The equation Eq. (2.1) as the equation of continuity in an adiabatic process determines such a cross-sectional area profile function $A_{HORN}(x)$ that triggers the enhanced de Laval jet-effect applied to the fluid tiny portion, associated with the acoustic wave (or the audible sound) entering the sound-inlet 2.A1 with the M-velocity of 1 Mach, higher than the specific M-velocity. The enhanced de Laval jet-effect, in particular, results in extra-acceleration of the laminar motion of the positive and negative changes in fluid density within the divergent horn 2.A at the expense of the fluid heat, understood in the wide sense including the concomitant turbulence inherently accompanying the acoustic wave.

Thus, the stages of the sound portion 2.A0 are as follows:

The sound portion 2.A0 enters the open sound-inlet 2.A1 with the conveying velocity $u_{convey}$ corresponding to the M-velocity of 1 Mach; it is the velocity of sound $u_{sound}$ when the sound is propagating in open space; then Within the divergent horn 2.A, the specific headway conveying motion of the fluid tiny portion becomes extra-accelerated due to the enhanced de Laval jet-effect; and then When the propagating sound, after crossing the open sound-outlet 2.A2, reaches the open space behind the open sound-outlet 2.A2 and becomes the launched sound beam 2.A3, the conveying M-velocity reverts back to 1 Mach corresponding to the velocity of sound $u_{sound}$ in the open space, wherein the acquired kinetic energy of the extra-accelerated specific headway conveying motion of the fluid tiny portion becomes transformed into the acquired wave power of the launched sound 2.A3 that, in turn, is manifested as the sound loudness boosting; namely, the integrated SPL of the launched sound 2.A3 is higher than the origin SPL of the entering sound portion 2.A0. Thus, the divergent horn 2.A is a waveguide that conveys the portion of sound 2.A0 generated by a source of sound 2.A10 to the set of sound detectors 2.A30 and provides for a high intensity of the conveyed sound beam 2.A3, higher than the intensity of the entering sound portion 2.A0. A feature of the embodiment 2.A of the divergent horn waveguide sound-booster is that the cross-sectional area $A_{OU}$ of the open sound-outlet 2.A2 is greater than the cross-sectional area $A_{IN}$ of the sound-inlet 2.A1; the higher the ratio $A_{OU}/A_{IN}$, the greater the increase in the acquired SPL of the sound subjected to the action of the divergent horn waveguide sound-booster 2.A.

In view of the foregoing description of the sub-paragraph "Optimized Horn For Gramophone" referring to FIG. 2 Case (A), it will be evident for a person who has studied the invention that:

on the one hand, the divergent horn 2.A is an optimal sound loudness booster, capable of conveying, widening, and boosting the entered sound beam 2.A0; and on the other hand, if a waveguiding to a relatively small detector of sound 2.A31 is required, a relatively enormous-huge sound-outlet is undesired.

Cascade of Optimized Horns

FIG. 2 Case (Cascade) shows schematically an embodiment 2.A40 performing a brokenly-cascaded waveguiding sound-booster constructed according to the principles of the present invention. The embodiment 2.A40 comprises a cascade of an in-line arranged multiplicity of N relatively-short slightly-divergent horns as acoustic nozzles (here, for the sake of simplicity and without loss of generality, N=3 relatively-short slightly-divergent horns are shown only): 2.A41, 2.A42, and 2.A43. The N relatively-short slightly-divergent horns: 2.A41, 2.A42, and 2.A43, denoted by the index n varying from 1 to N, have open sound-inlets: 2.A51, 2.A52, and 2.A53, having sound-inlets' cross-sectional areas $A_{IN,n}$, n=1, 2, ..., N, and open sound-outlets: 2.A61, 2.A62, and 2.A63, having sound-inlets' cross-sectional areas $A_{OU,n}$, n=1, 2, ..., N, correspondingly. There are certain intervals of open space 2.A71 and 2.A72 between intermediate open sound-inlets 2.A52 to 2.A53 and intermediate open sound-outlets 2.A61 to 2.A62, correspondingly, within the embodiment 2.A40. Thereby, the cascade 2.A40 of the in-line arranged multiplicity of N relatively-short slightly-divergent horns: 2.A41, 2.A42, and 2.A43, arranged with intervals of open space and considered as a whole, performs a broken through-hole tunnel-waveguide 2.A40, submerged in the molecular fluid and being exposed to a sound beam 2.A00 generated by a source of sound 2.A11. Each n-th of the N relatively-short slightly-divergent horns is recognized by a varying cross-sectional area characterized by a slightly-divergent cross-sectional area profile function $A_n(x)$, n=1, 2, ..., N, such that the embodiment 2.A40 as a whole is recognized by the geometrical configuration of the through-hole tunnel-waveguide broken with intervals of open space, wherein the geometrical configuration has a varying cross-sectional area characterized by a cross-sectional area profile function $A_{BROKEN}(x)$ specified as a piecewise-broken-with-intervals piecewise-divergent profile function of x comprising the N slightly-divergent portions $A_n(x)$. Each n-th of the N slightly-divergent portions $A_n(x)$ is expressed as $$A_n(x) = \frac{A_{*n}}{M_n(x)}\left(\frac{\gamma-1}{\gamma}\right)^{\frac{1}{2}}\left(\frac{2+\gamma(M_n(x))^2}{\gamma+1}\right)^{\frac{\gamma+1}{2(\gamma-1)}}, \quad \text{Eq. (2.2)}$$

$$x_{a,n} < x < x_{b,n}$$
$$n = 1, 2, \ldots, N$$

where the index n varies from 1 to N, $x_{a,n}$ and $x_{b,n}$ are x-coordinates of the open sound-inlet and open sound-outlet, correspondingly, of the n-th divergent horn, $\gamma$ is an adiabatic compressibility parameter of the fluid, and $M_n(x)$ is an n-th monotonically-increasing gradually-smooth function of x representing an M-velocity profile of the fluid tiny portion moving within and through the divergent horn.

The N equations Eq. (2.2), as the equations of continuity in an adiabatic process applied to the headway motion of the fluid tiny portions entering each of the sound-inlets 2.A51, 2.A52, and 2.A53 with the M-velocity of 1 Mach, higher than the specific M-velocity $M_* = \sqrt{(\gamma-1)/\gamma}$, altogether provide for a substantially laminar motion of the positive and negative changes in air density within each of the relatively-short slightly-divergent horns: 2.A41, 2.A42, and 2.A43 due to the enhanced de Laval jet-effect. Thus, the sound beam 2.A00:
  enters the sound-inlet 2.A51 of the first relatively-short slightly-divergent horn 2.A41, where, immediately after entering, the laminar motion of the positive and negative changes in air density becomes accelerated as a headway motion of fluid moving within a divergent pipe with the high M-velocity of 1 Mach, higher than the specific M-velocity $M_* = \sqrt{(\gamma-1)/\gamma}$;
  further propagates within and along the broken through-hole tunnel-waveguide 2.A40,
  sequentially reaches the intermediate intervals 2.A71 to 2.A72 where the propagating sound beam portions 2.A01 to 2.A02, correspondingly, become in open spaces and so become characterized with the conveying motion with the M-velocity of 1 Mach; wherein the intermediate intervals of the open spaces 2.A71 to 2.A72 can be chosen as extremely short in the direction of the sound propagation because the minor mass of the fluid tiny portion associated with the propagating sound is practically inertialess, and so, the open space M-velocity of sound, i.e. 1 Mach, is reachable in the open space almost immediately behind each of the intermediate open sound-outlets: 2.A61 to 2.A62; such that:
    on the one hand, when the propagating sound crosses the intervals of open space 2.A71 to 2.A72, the sequentially acquired portions of the kinetic energy of the accelerated specific headway conveying motion of the fluid tiny portion become transformed into the acquired wave power of the propagating sound beam portions 2.A01 to 2.A02, correspondingly, and
    on the other hand, the propagating sound beam portions 2.A01 to 2.A02 enter the open sound-inlets 2.A52 to 2.A53, correspondingly, with the M-velocity of 1 Mach, thereby always satisfying the condition of the entrance the open sound-inlet of a next relatively-short slightly-divergent horn with the M-velocity of 1 Mach;
  reaches the sound-outlet 2.A63 of the last relatively-short slightly-divergent horn 2.A43, and
  becomes the finally launched sound beam 2.A03 in open space behind the last sound-outlet 2.A63, where the cumulatively acquired portion of the kinetic energy of the accelerated specific headway conveying motion of the fluid tiny portion becomes transformed into the acquired wave power of the finally launched sound beam 2.A03.

In view of the foregoing description of the sub-paragraphs "Cascade Of Optimized Horns" referring to FIG. 2 Case (Cascade), it will be evident for a person who has studied the invention that:
  the cascade of the in-line arranged multiplicity of N relatively-short slightly-divergent horns 2.A40, arranged with intervals of open space and considered as a whole, is an optimized sound loudness booster, capable of conveying and amplifying the entered sound beam 2.A00; and
  if a waveguiding to a relatively small detector of sound 2.A31 is required, the use of the broken through-hole tunnel-waveguide 2.A40 is preferred to provide a slightly widened and substantially amplified resulting sound beam 2.A03.

Phonendoscope and Sound-Booster

FIG. 2 Cases (B) and (C) are schematic illustrations of two-stage convergent-divergent acoustic nozzles 2.B and 2.C, destined for amplifying the intensity of an entering portion of sound 2.B0 and 2.C0, correspondingly. The enhanced phonendoscope 2.B and sound booster 2.C, both constructed according to the principles of the present invention, comprise common configurational features as follows:
  the two-stage convergent-divergent acoustic nozzle playing the role of the sound-booster to be used as a phonendoscope having a configured corpus, 2.B1 or 2.C1, comprising a through-hole tunnel-waveguide, 2.B2 or 2.C2, wherein:
    a sound-inlet, 2.B5 or 2.C5, of a first convergent-divergent fragment has a cross-sectional area $A_{IN}$,
    a sound-outlet, 2.B6 or 2.C6, of a second convergent-divergent fragment has a cross-sectional area $A_{OU}$, and
    shaped portions of a varying cross-section recognized by:
      a convergent funnel, 2.B41 or 2.C41,
      the first narrow throat, 2.B42 or 2.C42, having a local minimal cross-sectional area $A_{TH1}$, a widened cavity, 2.B43 or 2.C43, having a local maximal cross-sectional area $A_{CA}$, the second narrow throat, 2.B44 or 2.C44, having the local minimal cross-sectional area $A_{TH2}$, wherein, theoretically, an optimal $A_{TH2}$ is equal to $A_{TH1}$, and in practice implementation, $A_{TH2}$ is at most equal to $A_{TH1}$, and divergent funnel, 2.B45 or 2.C45, and the cross-sectional area profile smooth function $A(x)$ is composed of sequentially concatenated cross-sectional area profile functions $A_1(x)$, $A_{CA}(x)$, and $A_2(x)$, wherein $A_1(x)$ and $A_2(x)$ are cross-sectional area profile functions of the first and second convergent-divergent fragments, which provide for the de Laval jet-effects, decelerating and accelerating the fluid tiny portion associated with the propagating sound, correspondingly, and $A_{CA}(x)$ is cross-sectional area profile function of the widened cavity providing for the enhanced Venturi effect while a gradually-smooth function $M_{CA}(x)$ of x, representing an M-velocity profile of the fluid tiny portion associated with the propagating sound and moving in the widened cavity between the first and second convergent-divergent fragments, remains lower than the specific M-velocity $M_*=\sqrt{(\gamma-1)/\gamma}$; the cross-sectional area profile functions $A_1(x)$ and $A_2(x)$ are given by the equations expressed as:

$$\begin{cases} A_1(x) = & x_{a,1} < x < x_{b,1} \\ \frac{A_{TH1}}{M_1(x)}\left(\frac{\gamma-1}{\gamma}\right)^{\frac{1}{2}}\left(\frac{2+\gamma(M_1(x))^2}{\gamma+1}\right)^{\frac{\gamma+1}{2(\gamma-1)}}, & \\ A_2(x) = & x_{a,2} < x < x_{b,2} \\ \frac{A_{TH2}}{M_2(x)}\left(\frac{\gamma-1}{\gamma}\right)^{\frac{1}{2}}\left(\frac{2+\gamma(M_2(x))^2}{\gamma+1}\right)^{\frac{\gamma+1}{2(\gamma-1)}}, & \end{cases} \quad \text{Eq. (2.3)}$$

where:

$\gamma$ is an adiabatic compressibility parameter of the fluid, $x_{a,1}$ and $x_{b,1}$ are x-coordinates of the open sound-inlet and open sound-outlet, correspondingly, of the first convergent-divergent fragment, $x_{a,2}$ and $x_{b,2}$ are x-coordinates of the open sound-inlet and open sound-outlet, correspondingly, of the second convergent-divergent fragment, $M_1(x)$ is a monotonically-decreasing gradually-smooth function of x, $M_2(x)$ is a monotonically-increasing gradually-smooth function of x, wherein $M_1(x)$, $M_{CA}(x)$, and $M_2(x)$ are sequentially-concatenated to form a gradually-smooth function $M(x)$ of x, representing an M-velocity profile of the fluid tiny portion moving within and through the two-stage convergent-divergent acoustic nozzle's through-hole tunnel-waveguide, 2.B2 or 2.C2;

and $A_{TH1}$ and $A_{TH2}$ are local minimal cross-sectional areas of narrow throats of the first and second convergent-divergent fragments, correspondingly;

wherein the satisfied conditions are as follows:
(a) the boundary condition at the sound-inlet $$\frac{A_{IN}}{A_{TH1}} \geq \sqrt{\left(\frac{\gamma-1}{\gamma}\right)\left(\frac{2+\gamma}{\gamma+1}\right)^{\frac{\gamma+1}{(\gamma-1)}}}; \quad \text{Eq. (2.3a)}$$

(b) the condition of presence of a widened cavity after the first convergent-divergent fragment $$A_{CA}/A_{TH1} > 1; \quad \text{Eq. (2.3b)}$$

(c) the condition of presence of a widened cavity before the second convergent-divergent fragment $$A_{CA}/A_{TH2} > 1; \quad \text{Eq. (2.3c)}$$

(d) the condition of proportion between cross-sectional areas of the two narrow throats of the two convergent-divergent fragments, $$A_{TH1}/A_{TH2} \geq 1, \quad \text{Eq. (2.3d)}$$

thereby providing for an acceleration of the fluid tiny portion moving within and through the second convergent-divergent fragment of the two-stage convergent-divergent acoustic nozzle's through-hole tunnel-waveguide, 2.B2 or 2.C2, such, to cross the second narrow throat, 2.B44 or 2.C44, with the specific M-velocity $M_*=\sqrt{(\gamma-1)/\gamma}$; and (e) the boundary condition at the sound-inlet, $$\frac{A_{OU}}{A_{TH2}} > \sqrt{\left(\frac{\gamma-1}{\gamma}\right)\left(\frac{2+\gamma}{\gamma+1}\right)^{\frac{\gamma+1}{(\gamma-1)}}}; \quad \text{Eq. (2.3e)}$$

While the two-stage convergent-divergent acoustic nozzle 2.B is configured to be used as an enhanced phonendoscope 2.B, the two-stage convergent-divergent acoustic nozzle 2.C is configured to have a corpus 2.C1 ergonomically adapted to a human's ear canal, thereby, allowing to be used as a sound booster 2.C ergonomically adapted to a human's ear 2.EAR.

The sound, 2.B0 or 2.C0, when entering the open sound-inlet, 2.B5 or 2.C5, becomes subjected to the action of the optimized convergent-divergent tunnel, 2.B2 or 2.C2, elaborated according to the equation Eq. (2.3) accompanied by the specific conditions Eqs. (2.3a) to (2.3e) interrelating the cross-sectional areas $A_{IN}$, $A_{OU}$, $A_{TH1}$, $A_{CA}$, and $A_{TH2}$ such that, first, when the sound, 2.B0 or 2.C0, propagates through a convergent funnel, 2.B41 or 2.C41, the sound intensity becomes:

on the one hand, decreased because the fluid tiny portion, being conveyed with the velocity of sound, becomes subjected to retarding due to the de Laval retarding-effect applied to the fluid tiny portion moving with the high velocity, higher than the specific M-velocity, and on the other hand, increased due to:
superposition of spatially distributed portions of sound becoming concentrated and joint in-phase, thereby, resulting in constructive interference,
transformation of the internal heat energy of fluid into the acquired power of sound, as a manifestation of the Venturi effect, applied to longitudinal oscillation motion with the particle velocity, and
suppression of concomitant turbulence, power of which, in the final analysis, becomes transformed into the acquired power of sound, as a phenomenon accompanying the Venturi effect applied to longitudinal oscillation motion with the particle velocity;

second, the condition Eq. (2.3a) is satisfied, and so the motion of the fluid tiny portion, when the sound propagates through the first narrow throat, 2.B42 or 2.C42, is decelerated and the sound intensity predetermined by the conveying velocity $U_{convey}$ is gradually decreasing due to the de Laval retarding-effect applied to the fluid tiny portion; wherein the local conveying M-velocity is equal to $M_*=\sqrt{(\gamma-1)/\gamma}$ when the fluid tiny portion crosses the narrowest cross-section within the first throat, 2.B42 or 2.C42;

third, the condition: $A_{IN}/A_{TH1}>1$ is satisfied and so, when the sound propagates through the first narrow throat 2.C42, the sound intensity predetermined by the particle velocity $u_{particle}$ is gradually increasing due to the Venturi effect applied to the slow-moving mass of fluid tiny portion of the fluid;

fourth, the condition: $A_{CA}/A_{TH1}>1$ Eq. (2.3b) is satisfied and so, when the sound propagates through the widened cavity, 2.B43 or 2.C43, the local conveying M-velocity becomes lower than the specific M-velocity $M_*$, due to the enhanced de Laval retarding-effect;

fifth the conditions:

$A_{CA}/A_{TH2} > 1$ and    Eq. (2.3c)

$A_{TH1}/A_{TH2} \geq 1$,    Eq. (2.3d)

both are satisfied and so, when the sound propagates through the second narrow throat, 2.B44 or 2.C44, the local conveying M-velocity reaches the specific M-velocity $M_*$, due to the enhanced de Laval jet-effect; and sixth, the conditions:

$A_{CA}/A_{TH2} > 1$ and    Eq. (2.3c)

$$\frac{A_{OU}}{A_{TH2}} > \sqrt{\left(\frac{\gamma-1}{\gamma}\right)\left(\frac{2+\gamma}{\gamma+1}\right)^{\frac{\gamma+1}{(\gamma-1)}}}$$    Eq. (2.3e)

both are satisfied and so, when the sound propagates further through divergent funnel, 2.B45 or 2.C45, the sound intensity becomes increased because the fluid tiny portion associated with the propagating sound, conveying with the varying velocity, becomes subjected to extra-acceleration due to the enhanced de Laval jet-effect applied to the fluid tiny portion moving with the high velocity, higher than the specific M-velocity and optimized to suppress turbulent component of the complicated movement of fluid when conveying the sound.

In view of the foregoing description of the sub-paragraphs "Optimized Horn For Gramophone" referring to FIG. 2 Case (A), "Cascade Of Optimized Horns" referring to FIG. 2 Case (Cascading), and "Phonendoscope and Sound Booster" referring to FIG. 2 Cases (B) and (C) compared with the description of sub-paragraphs: "Sound as Complicated Movement in Molecular Fluid" referring to prior art FIG. 1n and "External Ear" referring to prior art FIG. 1L, it becomes evident to a person who has studied the present patent application that, conceptually:

The external ear 1L.0 (FIG. 1L) functions as the described passive sound booster 2.C, but not optimized for suppression of concomitant turbulences according to the equation Eq. (2.3) accompanied by the associated requirements to the cross-sectional areas $A_{IN}$, $A_{TH1}$, $A_{CA}$, $A_{TH2}$, and $A_{OU}$ yet;

An optimized two-stage convergent-divergent acoustic nozzle, optimized for providing laminar motion of the fluid tiny portion according to the equation Eq. (2.3) and accompanied conditions Eqs. (2.3a) to (2.3e), can be adapted to a diversity of applications as a waveguiding and sound-amplifying nozzle for detectors or launchers of sound, for instance:

the optimized two-stage convergent-divergent acoustic nozzle 2.B can be utilized as a phonendoscope; and the optimized two-stage convergent-divergent acoustic nozzle 2.C can be ergonomically-adapted to a human's ear canal and play a role of a passive sound-booster utilized for amplifying the loudness of a portion of ambient sound;

An optimized divergent horn, optimized for widening a front of sound beam accompanied by suppression of concomitant turbulences according to the equation Eq. (2.1), can be scaled to play the role of an enhanced generalized gramophone utilized for boosting a sound launched by a source of acoustic waves; and An acoustic waveguide representing a cascade of the in-line arranged multiplicity of N relatively-short slightly-divergent horns, arranged with intervals of open space and considered as a whole, wherein the cross-sectional area of each of the of N relatively-short slightly-divergent horns is optimized and adapted to launch a sound beam of a certain sound-outlet cross-sectional shape and area according to a set of N equations Eq. (2.2) to provide conveying and boosting a sound at the expense of the heat of fluid and concomitant turbulences.

Sound-Silencer

FIG. 3, composed of two parts: Case (A) and Case (B), illustrates modifications of an enhanced sound-silencer. The modifications are passive devices having no moving parts designed in accordance with the principles of the present invention for suppression of sound loudness.

Optimized Sound Dissipator

FIG. 3 Cases (A) is a schematic illustration of a convergent-divergent acoustic nozzle 3.A destined for reducing the intensity of an entering portion of sound 3.A0 to function as an enhanced sound-silencer. The convergent-divergent acoustic nozzle 3.A comprises a shaped through-hole tunnel having a convergent-divergent sectional profile. The convergent-divergent acoustic nozzle 3.A, the geometrical configuration of which is designed in accordance with principles of the present invention, is submerged in a molecular fluid (for the sake of concretization and without loss of generality, the molecular fluid is air) and exposed to a portion of sound 3.A0 launched by a source of acoustic waves 3.A10. The portion of sound 3.A0:

enters an open sound-inlet 3.A1 having a cross-sectional area $A_{IN}$, propagates within the convergent-divergent acoustic nozzle 3.A through a narrow throat 3.A4 crossing a minimal cross-sectional area $A_{TH}$ at a critical condition point 3.A41, reaches the open sound-outlet 3.A2 having a cross-sectional area $A_{OU}$, becomes launched from the open sound-outlet 3.A2, where, in the open space, is detected by a set of acoustic wave detectors 3.A30.

Again, the specific conveying motion of the air density is interpreted as composed of two complementary alternating headway movements of positive and negative changes in air density, wherein both alternating headway movements are in the same direction (that is the direction of sound propagation) and, when the headway movements are in the open space, with the M-velocity of 1 Mach. When the sound portion 3.A0 propagates within the convergent-divergent acoustic nozzle 3.A, the specific conveying motion of the air density is subjected to the influence of bordering walls of the shaped through-hole tunnel 3.A. To provide for that the convergent-divergent acoustic nozzle 3.A functions as an enhanced sound-silencer destined for reducing the intensity of the entering portion of sound 3.A0, the geometrical configuration of the shaped through-hole tunnel 3.A is characterized by a varying cross-sectional area profile function $A_{SILENCER}(x)$ of x expressed as:

$$A_{SILENCER}(x) = \frac{A_{TH}}{M_{SILENCER}(x)} \left(\frac{\gamma-1}{\gamma}\right)^{\frac{1}{2}} \left(\frac{2+\gamma(M_{SILENCER}(x))^2}{\gamma+1}\right)^{\frac{\gamma+1}{2(\gamma-1)}}, \quad \text{Eq. (3.1)}$$

where $\gamma$ is an adiabatic compressibility parameter of the fluid and $M_{SILENCER}(x)$ is a monotonically-decreasing gradually-smooth function of x representing an M-velocity profile of the fluid tiny portion moving within and through the convergent-divergent acoustic nozzle 3.A, wherein the ratio of the cross-sectional area $A_{IN}$ of the nozzle's open sound-inlet 2.A1 to the local minimal cross-sectional area $A_{TH}$ satisfies to the condition:

$$\frac{A_{IN}}{A_{TH}} \geq \sqrt{\left(\frac{\gamma-1}{\gamma}\right)\left(\frac{2+\gamma}{\gamma+1}\right)^{\frac{\gamma+1}{(\gamma-1)}}}. \quad \text{Eq. (3.1a)}$$

The condition Eq. (3.1a) provides for triggering the enhanced de Laval retarding-effect applied to the fluid tiny portion entering the sound-inlet 3.A1 with the M-velocity of 1 Mach, higher than the specific M-velocity. The enhanced de Laval retarding-effect, in particular, results in extra-deceleration of the laminar motion of the positive and negative changes in air density within the convergent-divergent acoustic nozzle 3.A resulting in dissipation of the acoustic wave power into the air heat understood in the direct sense. Thus, the stages of the sound portion 3.A0 are as follows:

The sound portion 3.A0 enters the open sound-inlet 3.A1 with the conveying velocity $u_{convey}$ corresponding to the M-velocity of 1 Mach; it is the velocity of sound $u_{sound}$ when the sound is propagating in open space; then Within the convergent-divergent acoustic nozzle 3.A, the specific headway conveying motion of the fluid tiny portion becomes extra-decelerated due to the enhanced de Laval retarding-effect; and then When the propagating sound reaches the open space behind the open sound-outlet 3.A2 and becomes the launched sound beam 3.A3, the conveying M-velocity reverts back to 1 Mach corresponding to the velocity of sound $u_{sound}$ in the open space, wherein the dissipated and thereby reduced kinetic energy of the decelerated specific headway conveying motion of the fluid tiny portion becomes rebuilt at the expense of the brought acoustic wave power of the launched sound 3.A3 that is manifested as the sound silencing: i.e. the integrated SPL of the launched sound 3.A3 which is registered by a set of sound detectors 3.A30 is lower than the origin SPL of the entering sound portion 3.A0 because the energy portion of the entering sound portion 3.A0 is unrecoverably dissipated into the heat of fluid due to the enhanced de Laval retarding effect.

Thereby, the convergent-divergent acoustic nozzle 3.A is an optimized sound dissipator capable of transforming the acoustic wave power into the heat energy of fluid and provides for the launched sound beam 3.A3 of decreased intensity, decreased becoming lower than the intensity of the entering sound portion 3.A0. A further feature of the embodiment of the sound-silencer 3.A is that the greater the ratio $A_{OU}/A_{IN}$, the lower the integral SPL of the launched sound beam 3.A3.

In view of the foregoing description of the sub-paragraph "Optimized Sound Dissipator" referring to FIG. 3 Case (A), it will be evident for a person who has studied the invention that:

on the one hand, the convergent-divergent acoustic nozzle 3.A is an optimal sound-silencer, capable of dissipating the wave power of the entered sound beam 3.A0 into the heat of fluid; and on the other hand, if it is required to dissipate a sound of a relatively wide front, the use of a sound-silencer having a relatively small sound-inlet and a relatively enormous-huge sound-outlet is not suitable.

Cascade Of Optimized Sound-Silencers

FIG. 3 Case (B) shows schematically an embodiment 3.B40 constructed according to the principles of the present invention. The embodiment 3.B40 comprises a cascade of an in-line arranged multiplicity of N relatively-short slightly-convergent-divergent acoustic nozzles (here, for the sake of simplicity and without loss of generality, N=3 relatively-short slightly-convergent-divergent acoustic nozzles are shown only): 3.B41, 3.B42, and 3.B43. The N relatively-short slightly-convergent-divergent acoustic nozzles: 3.B41, 3.B42, and 3.B43, have open sound-inlets: 3.B51, 3.B52, and 3.B53, narrow throats: 3.B81, 3.B82, and 3.B83, recognized by minimal cross-sectional areas at positions: 3.B91, 3.B92, and 3.B93, and open sound-outlets: 3.B61, 3.B62, and 3.B63, correspondingly. There are certain intervals of open space 3.B71 and 3.B72 between intermediate open sound-inlets 3.B52 to 3.B53 and intermediate open sound-outlets 3.B61 to 3.B62, correspondingly, within the embodiment 3.B40. Thereby, the cascade 3.B40 of the in-line arranged multiplicity of relatively-short slightly-convergent-divergent acoustic nozzles: 3.B41, 3.B42, and 3.B43, arranged with intervals of open space and considered as a whole, performs a broken through-hole tunnel-wave-guide 3.B40, submerged in the molecular fluid and exposed to a sound beam 3.B00 generated by a source of sound 3.B10. The N relatively-short slightly-convergent-divergent acoustic nozzles are denoted by the index n varying from 1 to N; each n-th of the N relatively-short slightly-conevergent-divergent acoustic nozzles is recognized by a varying cross-sectional area characterized by a slightly-convergent-divergent cross-sectional area profile function $A_n(x)$, n=1, 2, ..., N, such that the embodiment 3.B40 as a whole is recognized by the geometrical configuration of the through-hole tunnel-waveguide broken with intervals of open space, wherein the geometrical configuration has a varying cross-sectional area characterized by a cross-sectional area profile function $A_{BROKEN}(x)$ specified as a piecewise-broken-with-intervals piecewise-convergent-divergent cross-sectional area profile function of x comprising the N slightly-convergent-divergent portions $A_n(x)$. Each n-th of the N slightly-convergent-divergent portions $A_n(x)$ is expressed as $$A_n(x) = \frac{A_{*n}}{M_n(x)}\left(\frac{\gamma-1}{\gamma}\right)^{\frac{1}{2}}\left(\frac{2+\gamma(M_n(x))^2}{\gamma+1}\right)^{\frac{\gamma+1}{2(\gamma-1)}}, \quad \text{Eq. (3.2)}$$

$$x_{a,n} < x < x_{b,n}$$
$$n = 1, 2, \ldots, N,$$

where the index n varies from 1 to N, $x_{a,n}$ and $x_{b,n}$ are x-coordinates of the open sound-inlet and open sound-outlet, correspondingly, of the n-th divergent horn, $\gamma$ is an adiabatic compressibility parameter of the fluid, $M_n(x)$ is an n-th monotonically-decreasing gradually-smooth function of x representing an M-velocity profile of the fluid tiny portion moving within and through the n-th slightly-convergent-divergent acoustic nozzle, and $A_{*n}$ is an n-th constant having a sense of the minimal cross-sectional area within the corresponding narrow throat, wherein the constant $A_{*n}$ is lesser than both a cross-sectional area $A_{IN,n}$ of the nozzle's sound-inlet 3.A51 and a cross-sectional area $A_{OU,n}$ of the nozzle's sound-outlet 3.A61, the ratio of the cross-sectional area $A_{IN,n}$ of the horn's sound-inlet 2.A1 to the constant $A_{*n}$ satisfies to the condition:

$$\frac{A_{IN,n}}{A_{*n}} \geq \sqrt{\left(\frac{\gamma-1}{\gamma}\right)\left(\frac{2+\gamma}{\gamma+1}\right)^{\frac{\gamma+1}{(\gamma-1)}}}, \quad n = 1, 2, \ldots, N, \quad \text{Eq. (3.2a)}$$

wherein the optimal ratio of the cross-sectional area $A_{IN,n}$ of the horn's sound-inlet 2.A1 to the constant $A_{*n}$ satisfies a condition as follows:

$$\frac{A_{IN,n}}{A_{*n}} = \sqrt{\left(\frac{\gamma-1}{\gamma}\right)\left(\frac{2+\gamma}{\gamma+1}\right)^{\frac{\gamma+1}{(\gamma-1)}}}, \quad n = 1, 2, \ldots, N. \quad \text{Eq. (3.2b)}$$

The conditions: Eq. (3.2) as the equation of continuity in an adiabatic process and Eq. (3.2b) for the optimal ratio $A_{IN,n}/A_{*n}$, both-together provide for a substantially laminar motion of the positive and negative changes in air density within each of the relatively-short slightly-convergent-divergent acoustic nozzles: 3.A41, 3.A42, and 3.A43 due to the enhanced de Laval retarding-effect applied to the moving positive and negative changes in air density, entering the nozzles with the high M-velocity of 1 Mach, higher than the specific M-velocity $M_*=\sqrt{(\gamma-1)/\gamma}$. The sound beam 3.A00:
- enters the sound-inlet 3.A51 of the first relatively-short slightly-convergent-divergent acoustic nozzle 3.A41, where,
- immediately after entering, the laminar motion of the positive and negative changes in air density becomes decelerated as a headway motion of fluid moving within a converging pipe with the high M-velocity of 1 Mach, higher than the specific M-velocity $M_*=\sqrt{(\gamma-1)/\gamma}$;
- when crossing the position 3.B91, the laminar motion of the positive and negative changes in air density is characterized by the specific M-velocity $M_*=\sqrt{(\gamma-1)/\gamma}$ and,
- downstream behind the position 3.B91, the laminar motion of the positive and negative changes in air density remains decelerating according to the enhanced de Laval retarding effect, wherein the laminarity of motion is provided by the conditions Eq. (3.2) and Eq. (3.2a);
- further propagates within and along the broken through-hole tunnel-waveguide 3.B40;
- sequentially reaches the intermediate intervals 3.B71 to 3.B72 where the propagating sound beam portions 3.B01 to 3.B02, correspondingly, become in open spaces and so become characterized with the conveying motion with the M-velocity of 1 Mach; wherein the intermediate intervals 3.B71 to 3.B72 of the open spaces can be chosen as extremely short because the minor mass of the fluid tiny portion associated with the propagating sound is practically inertialess and so, the open space M-velocity of sound, i.e. 1 Mach, is reachable in the open space immediately behind the intermediate open sound-outlets 3.B61 to 3.B62; such that:
  - on the one hand, the sequentially acquired portions of the kinetic energy of the accelerated specific headway conveying motion of the fluid tiny portion become transformed into the acquired wave power of the propagating sound beam portions 3.B01 to 3.B02, and
  - on the other hand, the propagating sound beam portions 3.B01 to 3.B02 enter the open sound-inlets 3.B52 and 3.B53 with the M-velocity of 1 Mach, thereby always satisfying the condition of the entrance the open sound-inlet of a next relatively-short slightly-convergent-divergent acoustic nozzle with the M-velocity of 1 Mach;
- reaches the sound-outlet 3.B63 of the last relatively-short slightly-convergent-divergent acoustic nozzle 3.B43, and
- becomes the finally launched sound beam 3.B03 in open space behind the last sound-outlet 3.B63, where the dissipated portion of the kinetic energy of the extra-decelerated specific headway conveying motion of the fluid tiny portion becomes rebuilt at the expense of the remained after the partial dissipation wave power of the finally launched sound beam 3.B03.

In view of the foregoing description of the sub-paragraphs "Cascade Of Optimized Sound-Silencers" referring to FIG. 3 Case (B), it will be evident for a person who has studied the invention that:
- the cascade of the in-line arranged multiplicity of N relatively-short slightly-convergent-divergent acoustic nozzles 3.B40, arranged with intervals of open space and considered as a whole, is an optimal sound-silencer, capable of dissipating the entered sound beam 3.B00; and
- if, from the point of view of a detector of sound 3.B30, sound isolation of the source of sound 3.B10 is required, the use of the broken through-hole tunnel-waveguide 3.B40 is preferred to provide a substantially dissipated resulting sound beam 3.B03.

In the claims, reference signs are used to refer to examples in the drawings for the purpose of easier understanding and are not intended to be limiting on the monopoly claimed.

The invention claimed is:

1. An acoustic nozzle [2.A, 2.B, 2.C, 3.A];
the acoustic nozzle comprising a solid corpus submerged in fluid and exposed to sound, audible or ultrasonic, propagating in the fluid; said solid corpus comprising an inner canal having:
  an open sound-inlet having a sound-inlet cross-sectional area, indicated by $A_{IN}$;
  an open sound-outlet having a sound-outlet cross-sectional area, indicated by $A_{OU}$; and
  a varying cross-sectional area, varying along the canal length, thereby, forming a shaped through-hole tunnel-waveguide being either converging, divergent, convergent-divergent, divergent-convergent, two-stage convergent-divergent;
wherein:
  an M-velocity is defined as a velocity measured in Mach numbers; and
  a sound is specified as a complicated movement of molecules of the fluid, wherein the complicated movement comprising motion components as follows:
    the Brownian motion of the molecules of the fluid;
    an oscillating motion of the molecules of the fluid, wherein the oscillation motion occurs with an oscillating particle velocity;
    a conveying motion of a tiny mass of the fluid in a direction of sound propagation; the tiny mass is the positive and negative changes in the mass density which is a result of the oscillating motion of the molecules, specifically synchronized in phase such that providing headway motion of the positive and negative changes in fluid mass density in the direction of the sound propagation, wherein the conveying motion of the tiny mass of the fluid occurring with a velocity of sound in the fluid; and
    turbulent motion of groups of the molecules of the fluid;
wherein:
  the open sound-inlet is exposed to ambient sound entering into and propagating within the inner canal and, thereby, the fluid within the shaped through-hole tunnel-waveguide is subjected to the propagating sound performing a complicated movement of the fluid;
  the shaped through-hole tunnel-waveguide is characterized by a cross-sectional area profile smooth function $A(x)$ of x-coordinates, where the x-coordinates are defined as increasing in a direction of sound propagation; wherein at least one portion, either converging, divergent, or convergent-divergent, of the shaped through-hole tunnel-waveguide, is characterized by a cross-sectional area profile function $A_{NOZZLE}(x)$, specified as a reference equation expressed as:

$$A_{NOZZLE}(x) = \frac{A_*}{M(x)}\left(\frac{\gamma-1}{\gamma}\right)^{\frac{1}{2}}\left(\frac{2+\gamma(M(x))^2}{\gamma+1}\right)^{\frac{\gamma+1}{2(\gamma-1)}}, x_a < x < x_b$$

where $\gamma$ is an adiabatic compressibility parameter of a portion of fluid, $x_a$ and $x_b$ are x-coordinates of the portion's beginning and end, correspondingly, $M(x)$ is a gradual smooth function of x representing a profile of an M-velocity of a tiny mass of the fluid motion within the shaped through-hole tunnel-waveguide, and $A_*$ is a constant satisfying a condition $$\frac{A_{IN}}{A_*} \geq \sqrt{\left(\frac{\gamma-1}{\gamma}\right)\left(\frac{2+\gamma}{\gamma+1}\right)^{\frac{\gamma+1}{(\gamma-1)}}};$$

thereby, providing for that the acoustic nozzle functions as either:
  a sound-booster, to:
    solve a problem of sound power dissipation into heat energy of fluid,
    convey the sound from the open sound-inlet to the open sound-outlet, and
    amplify loudness of the sound at the expense of both the heat energy of fluid and concomitant turbulence of the fluid;
  or, contrariwise,
  a sound-silencer, to suppress a waveguide effect and transform the sound's intensity into ambient heat thereby solving a problem of sound propagation.

2. A divergent horn sound-booster [2.A];
the divergent horn sound-booster comprising the acoustic nozzle of claim 1, wherein the inner canal is configured as a divergent pipe diverging from the open sound-inlet to the open sound-outlet, wherein the cross-sectional profile function $A(x)$ is further specified as a divergent cross-sectional profile function $A_{HORN}(x)$ derived from the reference equation restricted by condition $$\frac{A_{IN}}{A_*} = \sqrt{\left(\frac{\gamma-1}{\gamma}\right)\left(\frac{2+\gamma}{\gamma+1}\right)^{\frac{\gamma+1}{(\gamma-1)}}}$$

and expressed as an equation of horn:

$$A_{HORN}(x) = \frac{A_{IN}}{M_{HORN}(x)}\left(\frac{2+\gamma(M_{HORN}(x))^2}{2+\gamma}\right)^{\frac{\gamma+1}{2(\gamma-1)}}, x_a < x < x_b,$$

where $x_a$ and $x_b$ are x-coordinates of the open sound-inlet and open sound-outlet, correspondingly, and $M_{HORN}(x)$ is a monotonically-increasing gradually-smooth function of x representing an M-velocity profile of the fluid tiny portion moving within and through the divergent horn sound-booster.

3. A brokenly-cascaded waveguiding sound-booster [2.A40] comprising a broken through-hole tunnel-waveguide formed by an in-line arranged brokenly-cascaded array of a multiplicity of the divergent horn sound-boosters of claim 2; the brokenly-cascaded waveguiding sound-booster has:
  a broken corpus, broken by at least one open space, and the divergent horn sound-boosters, indicated by index n enumerated from 1 to N, wherein N is defined as at least 2;
wherein each n-th divergent horn sound-booster comprises:
  an open sound-inlet having a sound-inlet cross-sectional area of $A_{IN,n}$;

an open sound-outlet having a sound-outlet cross-sectional area of $A_{OU,n}$; a condition $A_{OU,n} > A_{IN,n}$ is satisfied; and a varying cross-sectional area, varying along the canal length thereby forming a shaped through-hole tunnel-waveguide being divergent and characterized by a cross-sectional area profile function $A_n(x)$;

wherein:

a cross-sectional area profile broken function of the waveguiding sound-booster as a whole is a piecewise-broken-with-intervals piecewise-divergent cross-sectional area profile function $A_{BROKEN}(x)$ comprising portions $A_n(x)$, n=1, 2, ..., N, associated with the n-th divergent horn sound-boosters, correspondingly, wherein the n-th cross-sectional area profile function $A_n(x)$ is expressed as:

$$A_n(x) = \frac{A_{IN,n}}{M_n(x)}\left(\frac{2+\gamma(M_n(x))^2}{2+\gamma}\right)^{\frac{\gamma+1}{2(\gamma-1)}},$$

$$x_{a,n} < x < x_{b,n},$$

$$n = 1, 2, \ldots, N,$$

where $x_{a,n}$ and $x_{b,n}$ are x-coordinates of the open sound-inlet and open sound-outlet, correspondingly, of the n-th divergent horn, and $M_n(x)$ is an n-th monotonically-increasing gradually-smooth function of x representing an M-velocity profile of the fluid tiny portion moving within and through the n-th divergent horn; and the N divergent horn sound-boosters are arranged sequentially one after another with intervals of open space such that a portion of the propagating sound sequentially:

enters the open sound-inlet of each n-th divergent horn sound-booster, propagates within the n-th divergent horn sound-booster, reaches the open sound-outlet of the n-th divergent horn sound-booster, becomes launched from the open sound-outlet of the n-th divergent horn sound-booster, while n<N, enters the interval of open space between the n-th and (n+1)-th divergent horn sound-boosters, and when n=N, becomes a resulting acoustic beam launched from the open sound-outlet of the N-th divergent horn sound-booster and characterized by an increased intensity manifested as boosted sound loudness.

4. A phonendoscope [2.B, 2.C];

the phonendoscope comprising the acoustic nozzle of claim 1, wherein the inner canal is configured as a two-stage convergent-divergent tunnel comprising three sequentially joint fragments as follows:

A first convergent-divergent fragment;

A divergent-convergent cavity; and

A second convergent-divergent fragment;

wherein:

said open sound-inlet having the sound-inlet cross-sectional area, indicated by $A_{IN}$, is an open sound-inlet of the first convergent-divergent fragment, said open sound-outlet having the sound-inlet cross-sectional area, indicated by $A_{OU}$, is an open sound-outlet of the second convergent-divergent fragment, and the divergent-convergent cavity has a local maximal cross-sectional area, indicated by $A_{CA}$;

the cross-sectional area profile smooth function $A(x)$ is composed of sequentially concatenated cross-sectional area profile functions $A_1(x)$, $A_{CA}(x)$, and $A_2(x)$, wherein:

$A_1(x)$ is cross-sectional area profile function of the first convergent-divergent fragment, which provides for the enhanced de Laval retarding-effect resulting in deceleration of the fluid tiny portion, $A_2(x)$ is cross-sectional area profile function of the second convergent-divergent fragment, which provides for the enhanced de Laval jet-effect resulting in acceleration of the fluid tiny portion, and the cross-sectional area profile functions $A_1(x)$ and $A_2(x)$ are given by the equations expressed as:

$$\begin{cases} A_1(x) = \frac{A_{TH1}}{M_1(x)}\left(\frac{\gamma-1}{\gamma}\right)^{\frac{1}{2}}\left(\frac{2+\gamma(M_1(x))^2}{\gamma+1}\right)^{\frac{\gamma+1}{2(\gamma-1)}}, & x_{a,1} < x < x_{b,1} \\ A_2(x) = \frac{A_{TH2}}{M_2(x)}\left(\frac{\gamma-1}{\gamma}\right)^{\frac{1}{2}}\left(\frac{2+\gamma(M_2(x))^2}{\gamma+1}\right)^{\frac{\gamma+1}{2(\gamma-1)}}, & x_{a,2} < x < x_{b,2} \end{cases}$$

where:

$x_{a,1}$ and $x_{b,1}$ are x-coordinates of the open sound-inlet and open sound-outlet, correspondingly, of the first convergent-divergent fragment, $x_{a,2}$ and $x_{b,2}$ are x-coordinates of the open sound-inlet and open sound-outlet, correspondingly, of the second convergent-divergent fragment, $M_1(x)$ is a monotonically-decreasing gradually-smooth function of x, $M_2(x)$ is a monotonically-increasing gradually-smooth function of x, and $A_{TH1}$ and $A_{TH2}$ are local minimal cross-sectional areas of narrow throats of the first and second convergent-divergent fragments, correspondingly;

$A_{CA}(x)$ is cross-sectional area profile function of the divergent-convergent cavity defined between $x_{b,1}$ and $x_{a,2}$ such that providing for the enhanced Venturi effect as a gradually-smooth function $M_{CA}(x)$ of x, representing an M-velocity profile of the tiny portion of the fluid moving in the divergent-convergent cavity between the first and second narrow throats, remains lower than the specific M-velocity $M_* = \sqrt{(\gamma-1)/\gamma}$;

$M_1(x)$, $M_{CA}(x)$, and $M_2(x)$ are sequentially-concatenated to form a gradually-smooth function $M(x)$ of x, representing an M-velocity profile of the fluid tiny portion moving within and through the two-stage convergent-divergent nozzle's through-hole tunnel-waveguide; and interrelations between the cross-sectional areas $A_{IN}$, $A_{TH1}$, $A_{CA}$, $A_{TH2}$, and $A_{OU}$ satisfying conditions as follows:

$$\frac{A_{IN}}{A_{TH1}} \geq \sqrt{\left(\frac{\gamma-1}{\gamma}\right)\left(\frac{2+\gamma}{\gamma+1}\right)^{\frac{\gamma+1}{(\gamma-1)}}}, \quad \text{(f)}$$

$$A_{CA} > A_{TH1}, \quad \text{(g)}$$

$$A_{CA} > A_{TH2}, \quad \text{(h)}$$

-continued $$A_{TH1} \geq A_{TH2}, \text{ and} \quad \text{(i)}$$

$$\frac{A_{OU}}{A_{TH2}} > \sqrt{\left(\frac{\gamma-1}{\gamma}\right)\left(\frac{2+\gamma}{\gamma+1}\right)^{\frac{\gamma+1}{(\gamma-1)}}}; \quad \text{(j)}$$

thereby providing for that, a portion of the propagating sound, entering the open sound-inlet, propagating through the two-stage convergent-divergent tunnel, and becoming launched from the open sound-outlet, becomes characterized by an amplified loudness.

5. The phonendoscope [2.C] of claim 4, wherein said solid corpus [2.C1] has an outer geometrical configuration ergonomically adapted to a human's ear, thereby providing that, when the open sound-inlet is exposed to ambient sound and the open sound-outlet is faced to an eardrum within the human's ear canal, the acoustic nozzle becomes capable of amplifying a loudness of a portion of sound yet to become entering the human's ear canal.

6. A sound-silencer [3.A];
 the sound-silencer comprising the acoustic nozzle of claim 1, wherein the inner canal is configured as a convergent-divergent pipe comprising:
  a converging funnel having the open sound-inlet [3.A1],
  a divergent exhaust tailpipe having the open sound-outlet [3.A2], and
  a narrow throat [3.A4] between the converging funnel and divergent exhaust tailpipe;
 wherein the cross-sectional profile function A(x) is further specified as a convergent-divergent cross-sectional profile function $A_{SILENCER}(x)$ expressed as:

$$A_{SILENCER}(x) = \frac{A_{*SILENCER}}{M_{SILENCER}(x)}\left(\frac{\gamma-1}{\gamma}\right)^{\frac{1}{2}}\left(\frac{2+\gamma(M_{SILENCER}(x))^2}{\gamma+1}\right)^{\frac{\gamma+1}{2(\gamma-1)}},$$

$$x_a < x < x_b$$

where $x_a$ and $x_b$ are x-coordinates of the open sound-inlet and open sound-outlet, correspondingly, $M_{SILENCER}(x)$ is a monotonically-decreasing gradually-smooth function of x representing an M-velocity profile of the fluid tiny portion moving within and through the convergent-divergent sound-silencer, and $A_{*SILENCER}$ is a constant, being lesser than both the cross-sectional area of the open sound-inlet $A_{IN}$ and the cross-sectional area of the open sound-outlet $A_{OU}$ and having a sense of a minimal cross-sectional area of the narrow throat between the converging funnel and divergent exhaust tailpipe, wherein the condition $$\frac{A_{IN}}{A_{*SILENCER}} = \sqrt{\left(\frac{\gamma-1}{\gamma}\right)\left(\frac{2+\gamma}{\gamma+1}\right)^{\frac{\gamma+1}{(\gamma-1)}}}$$

is satisfied.

7. A brokenly-cascaded sound-silencer [3.B40] comprising a broken pipe formed by an in-line arranged brokenly-cascaded array of a multiplicity of the sound-silencer of claim 6;
 the brokenly-cascaded sound-silencer has:
  a broken corpus, broken by at least one open space, and the sound-silencers, indicated by index n enumerated from 1 to N, wherein N is defined as at least 2;
 wherein each n-th sound-silencer comprises:
  an open sound-inlet having a sound-inlet cross-sectional area of $A_{IN,n}$;
  an open sound-outlet having a sound-outlet cross-sectional area of $A_{OU,n}$; and
  a varying cross-sectional area, varying along the canal length thereby forming a shaped pipe being convergent-divergent and characterized by a cross-sectional area profile function $A_n(x)$;
 wherein:
  a cross-sectional area profile broken function of the brokenly-cascaded sound-silencer as a whole is a piecewise-broken-with-intervals piecewise-convergent-divergent cross-sectional area profile function $A_{BROKEN}(x)$ comprising portions $A_n(x)$, n=1, 2, . . . , N, associated with the n-th sound-silencer, correspondingly, wherein the n-th cross-sectional area profile function $A_n(x)$ is expressed as:

$$A_n(x) = \frac{A_{*n}}{M_n(x)}\left(\frac{\gamma-1}{\gamma}\right)^{\frac{1}{2}}\left(\frac{2+\gamma(M_n(x))^2}{\gamma+1}\right)^{\frac{\gamma+1}{2(\gamma-1)}},$$

$$x_{a,n} < x < x_{b,n}$$

$$n = 1, 2, \ldots, N$$

where $x_{a,n}$ and $x_{b,n}$ are x-coordinates of the open sound-inlet and open sound-outlet, correspondingly, of the n-th sound-silencer, and $M_n(x)$ is an n-th monotonically-decreasing gradually-smooth function of x representing an M-velocity profile of the fluid tiny portion moving within and through the n-th sound-silencer; and the N sound-silencers are arranged sequentially one after another with intervals of open space such that a portion of the propagating sound sequentially:
 enters the open sound-inlet of each n-th sound-silencer,
 propagates within the n-th sound-silencer,
 reaches the open sound-outlet of the n-th sound-silencer,
 becomes launched from the open sound-outlet of the n-th sound-silencer,
 while n<N, enters the interval of open space between the n-th and (n+1)-th sound-silencer, and
 when n=N, becomes a resulting acoustic beam launched from the open sound-outlet of the N-th sound-silencer and characterized by a decreased intensity manifested as suppressed sound loudness.

* * * * *